United States Patent
Wu et al.

(10) Patent No.: US 12,431,242 B2
(45) Date of Patent: Sep. 30, 2025

(54) POWER EFFICIENT AGENT MONITORING DEVICES AND METHODS

(71) Applicant: Huawei Technologies Co., Ltd., Guandong (CN)

(72) Inventors: Jialing Wu, Lebanon, NH (US); Yingxuan Zhu, Framingham, MA (US); Han Su, Framingham, MA (US); Jian Li, Newton, MA (US)

(73) Assignee: Huawei Technologies Co., Ltd., Shenzhen (CN)

( * ) Notice: Subject to any disclaimer, the term of this patent is extended or adjusted under 35 U.S.C. 154(b) by 193 days.

(21) Appl. No.: 18/177,059

(22) Filed: Mar. 1, 2023

(65) Prior Publication Data
US 2023/0207120 A1 Jun. 29, 2023

Related U.S. Application Data

(63) Continuation of application No. PCT/US2020/049060, filed on Sep. 2, 2020.

(51) Int. Cl.
*G16H 40/67* (2018.01)
*G06N 3/0442* (2023.01)
*G16H 40/40* (2018.01)

(52) U.S. Cl.
CPC ........... *G16H 40/67* (2018.01); *G06N 3/0442* (2023.01); *G16H 40/40* (2018.01)

(58) Field of Classification Search
CPC ......... G16H 40/40; G16H 40/67; G06N 20/00
See application file for complete search history.

(56) References Cited

U.S. PATENT DOCUMENTS

| | | | |
|---|---|---|---|
| 2012/0083237 A1* | 4/2012 | Fish | G01P 1/07 455/404.1 |
| 2014/0247146 A1* | 9/2014 | Proud | H02J 50/10 340/870.02 |

(Continued)

FOREIGN PATENT DOCUMENTS

EP 3579084 A1 * 12/2019 ............. A61B 5/002

OTHER PUBLICATIONS

Kim, Y., et al., "Resource-Efficient Pet Dog Sound Events Classification Using LSTM-FCN Based on Time-Series Data," Sensors 2018, 18, 4019; doi:10.3390/s18114019, www.mdpi.com/journal/sensors, Nov. 18, 2018, 17 pages.

(Continued)

*Primary Examiner* — Raymond N Phan
(74) *Attorney, Agent, or Firm* — Conley Rose, P.C.

(57) ABSTRACT

A method implemented by an agent monitoring device, comprises obtaining, by a sensor of the agent monitoring device, sensor data over a period of time, the sensor data describing a characteristic of an agent associated with the agent monitoring device, determining output data for the sensor based on the sensor data using a learning model, determining a sensor condition for the sensor, determining that a power level of a battery of the agent monitoring device meets the pre-defined power level, determining whether the output data meets the threshold value of the sensor condition in response to the power level of the battery having reached the pre-defined power level, and uploading an indication of the output data to at least one of a cloud server or a representative device in response to the output data for the sensor having met the threshold value of the sensor condition.

20 Claims, 10 Drawing Sheets

(56) References Cited

U.S. PATENT DOCUMENTS

2019/0197236 A1* 6/2019 Niculescu-Mizil ... G06F 21/554
2020/0379454 A1* 12/2020 Trinh ................... G05B 23/024
2021/0057920 A1* 2/2021 Husain .............. H02J 13/00002
2022/0019863 A1* 1/2022 Iskandar ................. G06F 18/15

OTHER PUBLICATIONS

Belda, B., et al., "Initial evaluation of PetPace activity monitor," The Veterinary Journal 237 (2018) 63-68, 2018, 6 pages.
Wang, W., et al., "Social Sensing: Assessing Social Functioning of Patients Living with Schizophrenia using Mobile Phone Sensing," 2020 Association of Computing Machinery, CHI 2020, Apr. 25-30, 2020, 15 pages.
Wang, W., et al., "Sensing Behavioral Change over Time: Using Within-Person Variability Features from Mobile Sensing to Predict Personality Traits," Proc. ACM Interact. Mob. Wearable Ubiquitous Technol., vol. 2, No. 3, Article 141, Sep. 2018, 21 pages.

\* cited by examiner

POWER EFFICIENT AGENT MONITORING DEVICES AND METHODS

CROSS-REFERENCE TO RELATED APPLICATIONS

The present application is a continuation of International Patent Application PCT/US2020/049060 filed Sep. 2, 2020 by Futurewei Technologies, Inc., entitled "Power Efficient Agent Monitoring Devices and Methods," which is hereby incorporated by reference as if reproduced in its entirety.

FIELD OF INVENTION

The present disclosure pertains to the field of monitoring devices and systems. In particular, the present disclosure relates to methods and devices for conserving power on a monitoring device.

BACKGROUND

Human beings of good health can easily communicate relevant information as needed with family, friends, and physicians. For example, a person can provide detailed symptoms to a physician when the person is not feeling well. Further, most people are generally aware enough to be able to make a phone call, or take remedial action, when they feel lost or in a dangerous situation.

However, some people, such as elderly people, infants, and toddlers, find it difficult to communicate. Further, they may not be aware enough to communicate symptoms or take remedial action, when necessary. Similarly, animals or pets also cannot communicate symptoms or take any actions that might be necessary to avoid a dangerous situation.

Monitoring devices have been introduced to track a pet's locations or monitor an elderly person's vital signs. However, current monitoring devices utilize a large amount of power to constantly monitor and upload the location and vital signs of the person or the pet being monitored. Further, these monitoring devices are generically configured to track the locations and monitor the vital signs for all the people or pets being monitored, without any specific regard to the person or pet actually being monitored.

SUMMARY

According to a first aspect of the present disclosure, there is provided a method implemented by an agent monitoring device, comprising obtaining, by a sensor of the agent monitoring device, sensor data over a period of time, the sensor data describing a characteristic of an agent associated with the agent monitoring device, determining, by a processor of the agent monitoring device, output data for the sensor based on the sensor data using a learning model, the output data being a value representing a predicted condition of the agent, the predicted condition being at least one of a physical condition, mental condition, behavior, or feature of the agent, updating, by the processor, the learning model using the output data, determining, by the processor, a sensor condition for the sensor, the sensor condition indicating a pre-defined power level and a threshold value, determining, by the processor, that a power level of a battery of the agent monitoring device meets the pre-defined power level, determining, by the processor, whether the output data meets the threshold value of the sensor condition in response to the power level of the battery having reached the pre-defined power level, and uploading, by a transmitter of the agent monitoring device, an indication of the output data to at least one of a cloud server or a representative device in response to the output data for the sensor having met the threshold value of the sensor condition.

Optionally, in a first implementation according to the first aspect, the learning model is based on a long short term memory (LSTM) architecture and on training data describing a behavior of a plurality of different agents similar to the agent, wherein the method further comprises receiving, by a receiver of the agent monitoring device, an update to the learning model from a cloud server, wherein the update to the learning model is based on the training data, and updating, by the processor, the learning model based on the update to the learning model to improve an accuracy of the learning model, wherein the sensor data is an input of the learning model, and wherein the output data is an output of the learning model.

Optionally, in a second implementation according to the first aspect or any other implementation of the first aspect, the method further comprises determining, by the processor, whether the power level of the battery meets a second pre-defined power level, and wherein, in response to the power level of the battery having reached the second pre-defined power level, the method further comprises powering off the sensor.

Optionally, in a third implementation according to the first aspect or any other implementation of the first aspect, the method further comprises determining, by the processor, standard data for the sensor, the standard data indicating a baseline behavior of the agent, and wherein, in response to the power level of the battery having reached the pre-defined power level, the method further comprises computing, by the processor, a difference between the output data and the standard data for the sensor, and uploading, by the transmitter, the output data to at least one of the cloud server or the representative device in response to the difference between the output data and the standard data having met the sensor condition.

Optionally, in a fourth implementation according to the first aspect or any other implementation of the first aspect, the method further comprises, after obtaining the sensor data over the period of time and before determining the output data, the method further comprises filtering, by the processor, the sensor data to remove noise unrelated to the agent, and performing, by the processor, normalization and interpolation of the sensor data.

Optionally, in a fifth implementation according to the first aspect or any other implementation of the first aspect, the agent monitoring device comprises a plurality of sensors that are each configured to detect a different type of sensor data, wherein the plurality of sensors comprise at least one of a Global Positioning System (GPS) locator, a BLUETOOTH device, a microphone, a thermometer, or a heart rate monitor, and wherein the different type of sensor data describes at least one of a temperature of the agent, a pulse of the agent, a calorie burn of the agent, a heart rate of the agent, a respiration activity of the agent, a physical activity of the agent, a sound emitted by the agent, a posture of the agent, a sleep activity of the agent, a GPS location of the agent, or a light surrounding the agent.

Optionally, in a sixth implementation according to the first aspect or any other implementation of the first aspect, each of the sensors is associated with a respective sensor condition, wherein the method further comprises obtaining, by the processor, different sensor data from each of the sensors, and determining, by the processor, output data for each of the sensors using the learning model, and wherein, in response to the power level of the battery having reached the pre-defined power level, the method further comprises determining, by the processor, that none of the output data for the sensors meets the respective sensor condition, determining, by the processor, aggregate sensor output data based on the output data for each of the sensors, a sensor weight for each of the sensors, a difference between sensor output data for each of the sensors and a standard data for each of the sensors, and uploading, by the transmitter, an indication of the aggregate sensor output data to at least one of the cloud server or the representative device in response to the aggregate sensor output data having met an aggregate condition.

Optionally, in a seventh implementation according to the first aspect or any other implementation of the first aspect, the learning model is based on training data describing a behavior of a plurality of different agents similar to the agent and a set of demographics describing the agent, and wherein the set of demographics describes at least one of a species, an age, or a gender of the agent.

According to a second aspect of the present disclosure, there is provided an agent monitoring device, comprising a sensor configured to obtain sensor data over a period of time, the sensor data describing a characteristic of an agent associated with the agent monitoring device, a memory configured to store instructions, and a processor coupled to the memory and configured to execute the instructions, which cause the processor to be configured to determine output data for the sensor based on the sensor data using a learning model, the output data being a value representing a predicted condition of the agent, the predicted condition being at least one of a physical condition, mental condition, behavior, or feature of the agent, update the learning model using the output data, determine a sensor condition for the sensor, the sensor condition indicating a pre-defined power level and a threshold value, determine that a power level of a battery of the agent monitoring device meets the pre-defined power level, determine whether the output data meets the threshold value of the sensor condition in response to the power level of the battery having reached the pre-defined power level, and upload an indication of the output data to at least one of a cloud server or a representative device in response to the output data for the sensor having met the threshold value of the sensor condition.

Optionally, in a first implementation according to the second aspect, the learning model is based on a long short term memory (LSTM) architecture and on training data describing a behavior of a plurality of different agents similar to the agent, wherein the instructions further cause the processor to be configured to receive an update to the learning model from a cloud server, wherein the update to the learning model is based on the training data, and update the learning model based on the update to the learning model to improve an accuracy of the learning model, wherein the sensor data is an input of the learning model, and wherein the output data is an output of the learning model.

Optionally, in a second implementation according to the second aspect or any other implementation of the second aspect, the instructions further cause the processor to be configured to determine whether the power level of the battery meets a second pre-defined power level, and wherein, in response to the power level of the battery having reached the second pre-defined power level, the instructions further cause the processor to be configured to power off the sensor.

Optionally, in a third implementation according to the second aspect or any other implementation of the second aspect, the instructions further cause the processor to determine standard data for the sensor, the standard data indicating a baseline behavior of the agent, and wherein, in response the power level of the battery having reached the pre-defined power level, the instructions further cause the processor to be configured to compute a difference between the output data and the standard data for the sensor, and wherein the memory is configured to store the output data in response to the difference between the output data and the standard data failing to meet the sensor condition.

Optionally, in a fourth implementation according to the second aspect or any other implementation of the second aspect, the instructions further cause the processor to be configured to filter the sensor data to remove noise unrelated to the agent, and perform normalization and interpolation of the sensor data.

Optionally, in a fifth implementation according to the second aspect or any other implementation of the second aspect, the agent monitoring device comprises a plurality of sensors that are each configured to detect a different type of sensor data, wherein the plurality of sensors comprise at least one of a GPS locator, a BLUETOOTH device, a microphone, a thermometer, or a heart rate monitor, and wherein the different type of sensor data describes at least one of a temperature of the agent, a pulse of the agent, a calorie burn of the agent, a heart rate of the agent, a respiration activity of the agent, a physical activity of the agent, a sound emitted by the agent, a posture of the agent, a sleep activity of the agent, a Global Positioning System (GPS) location of the agent, or a light surrounding the agent.

According to a third aspect of the present disclosure, there is provided a computer program product comprising computer-executable instructions for storage on a non-transitory computer-readable medium that, when executed by a processor, cause an agent monitoring device to obtain sensor data over a period of time, the sensor data describing a characteristic of an agent associated with the agent monitoring device, determine output data for the sensor based on the sensor data using a learning model, the output data being a value representing a predicted condition of the agent, the predicted condition being at least one of a physical condition, mental condition, behavior, or feature of the agent, update the learning model using the output data, determine a sensor condition for the sensor, the sensor condition indicating a pre-defined power level and a threshold value, determine that a power level of a battery of the agent monitoring device meets the pre-defined power level, determine whether the output data meets the threshold value of the sensor condition in response to the power level of the battery having reached the pre-defined power level, and upload an indication of the output data to at least one of a cloud server or a representative device in response to the output data for the sensor having met the threshold value of the sensor condition.

Optionally, in a first implementation according to the third aspect, the learning model is based on a long short term memory (LSTM) architecture and on training data describing a behavior of a plurality of different agents similar to the agent, wherein the computer-executable instructions further cause the agent monitoring device to receive an update to the learning model from a cloud server, wherein the update to the learning model is based on the training data, and update the learning model based on the update to the learning model to improve an accuracy of the learning model, wherein the sensor data is an input of the learning model, and wherein the output data is an output of the learning model.

Optionally, in a second implementation according to the third aspect or any other implementation of the third aspect, the computer-executable instructions further cause the agent monitoring device to determine whether the power level of the battery meets a second pre-defined power level, and wherein, in response to the power level of the battery having reached the second pre-defined power level, the computer-executable instructions further cause the agent monitoring device to power off the sensor.

Optionally, in a third implementation according to the third aspect or any other implementation of the third aspect, the computer-executable instructions further cause the agent monitoring device to determine standard data for the sensor, the standard data indicating a baseline behavior of the agent, and wherein, in response to the power level of the battery having reached the pre-defined power level, the computer-executable instructions further cause the agent monitoring device to compute a difference between the output data and the standard data for the sensor, and upload the indication of the output data to at least one of the cloud server or the representative device in response to the difference between the output data and the standard data having met the sensor condition.

Optionally, in a fourth implementation according to the third aspect or any other implementation of the third aspect, the agent monitoring device comprises a plurality of sensors that are each configured to detect a different type of sensor data, wherein the plurality of sensors comprise at least one of a GPS locator, a BLUETOOTH device, a microphone, a thermometer, or a heart rate monitor, and wherein the different type of sensor data describes at least one of a temperature of the agent, a pulse of the agent, a calorie burn of the agent, a heart rate of the agent, a respiration activity of the agent, a physical activity of the agent, a sound emitted by the agent, a posture of the agent, a sleep activity of the agent, a Global Positioning System (GPS) location of the agent, or a light surrounding the agent.

Optionally, in a fifth implementation according to the third aspect or any other implementation of the third aspect, each of the sensors is associated with a respective sensor condition, wherein the computer-executable instructions further cause the agent monitoring device to obtain different sensor data from each of the sensors, and determine output data for each of the sensors using the learning model, wherein, in response the power level of the battery having reached the pre-defined power level, the computer-executable instructions further cause the agent monitoring device to determine that none of the output data for the sensors meets the respective sensor condition, determine aggregate sensor output data based on the output data for each of the sensors, a sensor weight for each of the sensors, a difference between sensor output data for each of the sensors and a standard data for each of the sensors, and upload an indication of the aggregate sensor output data to at least one of the cloud server or the representative device in response to the aggregate sensor output data having met an aggregate condition.

According to a third aspect of the present disclosure, there is provided an apparatus comprising a means for obtaining sensor data over a period of time, the sensor data describing a characteristic of an agent associated with the agent monitoring device, a means for determining output data for the sensor based on the sensor data using a learning model, the output data being a value representing a predicted condition of the agent, the predicted condition being at least one of a physical condition, mental condition, behavior, or feature of the agent, a means for updating the learning model using the output data, a means for determining a sensor condition for the sensor, the sensor condition indicating a pre-defined power level and a threshold value, a means for determining that a power level of a battery of the apparatus meets the pre-defined power level, a means for determining whether the output data meets the threshold value of the sensor condition in response to the power level of the battery having reached the pre-defined power level, and a means for uploading an indication of the output data to at least one of a cloud server or a representative device in response to the output data for the sensor having met the threshold value of the sensor condition.

These and other features will be more clearly understood from the following detailed description taken in conjunction with the accompanying drawings and claims.

BRIEF DESCRIPTION OF THE DRAWINGS

For a more complete understanding of this disclosure, reference is now made to the following brief description, taken in conjunction with the accompanying drawings and detailed description, wherein like reference numerals represent like parts.

DETAILED DESCRIPTION

Figure 1:
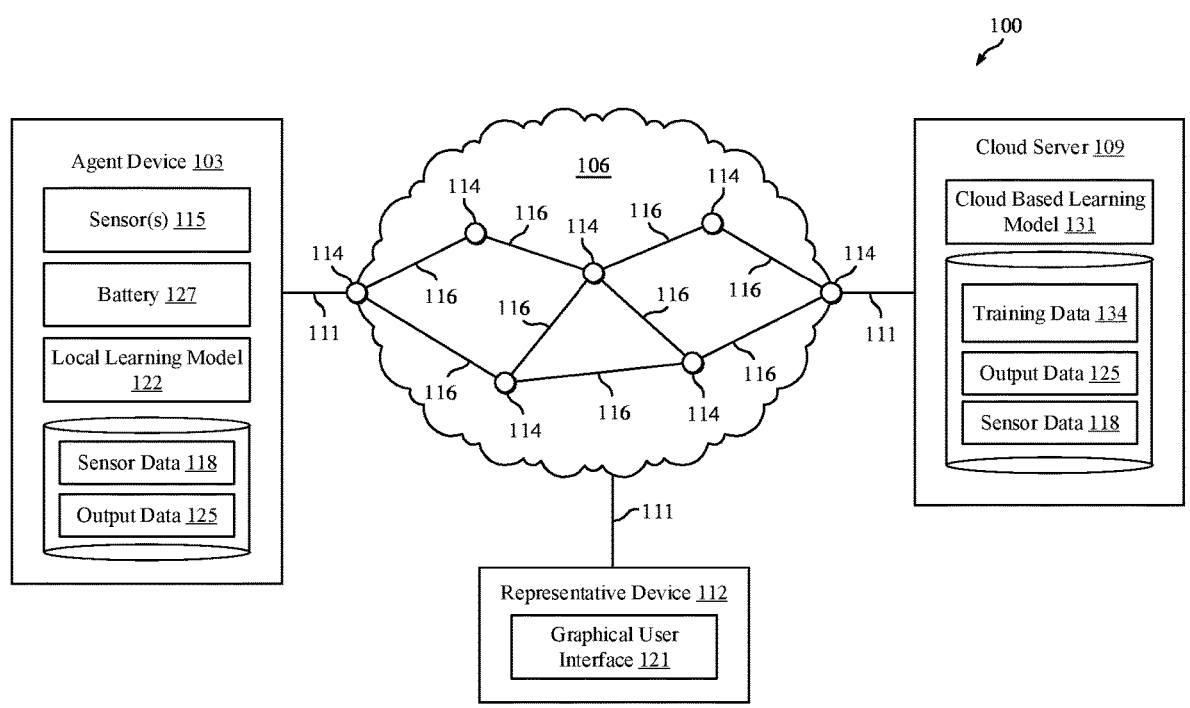
FIG. 1 is a diagram illustrating an agent monitoring system configured to implement power efficient methods of monitoring an agent according to various embodiments of the disclosure.

It should be understood at the outset that although an illustrative implementation of one or more embodiments are provided below, the disclosed systems and/or methods may be implemented using any number of techniques, whether currently known or in existence. The disclosure should in no way be limited to the illustrative implementations, drawings, and techniques illustrated below, including the exemplary designs and implementations illustrated and described herein, but may be modified within the scope of the appended claims along with their full scope of equivalents.

As described above, monitoring devices utilize a great amount of power and computing resources to collect information about an agent (e.g., the person or animal being monitored) and upload the information to a representative of the agent (e.g., owner of the animal or family member of the person). For example, monitoring devices constantly and unintelligently collect data regarding the agent and upload the collected data to a server or to a device belonging to the representative of the agent. These monitoring devices consume a heavy amount of computing resources to constantly collect and upload this data, which in turn quickly drains the battery of the monitoring device.

Further, these monitoring devices are generalized for agents, and may only vary depending on whether the agent is a human or a type of animal. For example, all dogs may be provided with the same type of monitoring device (e.g., dog collar), and all elderly people are provided with the same type of monitoring device (e.g., smart watch, skin patch, wearable sensors etc.). However, different types of dogs may need to be monitored differently, or dogs of different ages may need to be monitored differently. Similarly, different people may have different baseline biometric characteristics, which require that they each monitored differently.

Disclosed herein are embodiments for power efficient methods of monitoring an agent while customizing how the agent is monitored according to learned characteristics of the agent. In some embodiments, an agent wears or carries around an agent device. The agent device includes multiple different types of sensors that each collects sensor data describing different characteristics of the agent over a period of time.

The sensor data is provided as an input into a machine learning model (referred to hereinafter as "the learning model"), which is generated using a long short-term memory recurrent neural network (RNN). The learning model implemented by the long short-term memory RNN uses the sensor data to generate output data describing a condition, feature, or behavior of the agent. The learning model is based on training data that describes other agents similar to the agent being monitored, and training data that describes the agent being monitored.

As the power level of a battery on the agent device decreases, the agent device differentially uploads the sensor data to a cloud server or a representative device. For example, the agent device reduces the amount of data transmitted out of the agent device as the power level of the battery decreases.

Therefore, the embodiments disclosed herein increase the battery life of the agent device by intelligently decreasing the amount of resources consumed by the agent device over time. By increasing the battery life of the agent device, the embodiments disclosed herein also lengthen the amount of the time for a representative of the agent to locate the agent and/or provide assistance to the agent. Further, the embodiments disclosed herein provide a customized agent device for different agents, thereby enabling a more accurate prediction of the conditions, features, or behaviors of the agent over time.

FIG. 1 is a diagram of an agent monitoring system 100 configured to implement power efficient methods of monitoring an agent according to various embodiments of the disclosure. As shown by FIG. 1, system 100 includes an agent device 103, a cloud server 109, and a representative device 112, each interconnected by a network 106. As should be appreciated, system 100 may include other components not otherwise shown in FIG. 1. System 100 may be configured to monitor an agent wearing the agent device 103 to obtained data, which is uploaded to the cloud server 109 or the representative device 112 in a power efficient manner, as will be further discussed below.

The network 106 is a network infrastructure that comprises a plurality of network nodes 114 that interconnect the agent device 103, cloud server 109, and representative device 112. The network 106 may be a packet network configured to support transporting of both the software components and data that may be used to perform the agent monitoring methods according to the embodiments disclosed herein. The network 106 is configured to implement network configurations to configure flow paths or virtual connections between the agent device 103, the cloud server 109, and the representative device 112. The network 106 may be a backbone network that connects the agent device 103, the cloud server 109, and the representative device 112. The network 106 may also connect the agent device 103, the cloud server 109, and the representative device 112 to other systems such as the external Internet, other cloud computing systems, data centers, and any other entity that accesses the cloud server 109.

The network nodes 114 may be routers, bridges, gateways, virtual machines, and/or any other type of node that is configured for packet forwarding. The network nodes 114 may be interconnected using links 116. The links 116 may be virtual links, which are logical paths between the network nodes 114, or physical links. The network nodes 114 may be interconnected using any suitable virtual link or physical link as should be appreciated by one of ordinary skill in the art. Links 111 may be wired or wireless links interconnecting an edge network node 114 positioned at the edge of network 106 with the agent device 103, the cloud server 109, and the representative device 112.

In an embodiment, the agent device 103 may be a user device, such as, for example, a wearable device, a mobile phone, a mobile tablet, an Internet of Things (IoT) device, a personal computer, or any device having access to memory and processing power. The agent device 103 comprises a battery 127 and one or more sensors 115. Each of the sensors 115 is configured to obtain sensor data 118 describing a characteristic of an agent wearing or carrying the agent monitoring device 103.

As used herein, the term "agent" refers to a person, an animal, a machine, a robot, or any other entity that may be monitored using the agent device 103. For example, the agent may be a pet (e.g., dog or cat) or an elderly person with difficulty communicating due to a cognitive decline illness. In the case where the agent is a pet, the agent device 103 may be embedded into a collar of the pet, such that the sensors 115 are placed on the pet at a location that facilitates monitoring, for example, vital signs of the pet as well as a location of the pet.

In an embodiment, the sensors 115 may include, for example, a Global Positioning System (GPS) locator, an altimeter, a BLUETOOTH device, a microphone, a thermometer, a pulse oximeter, a heart rate monitor, a camera, an accelerometer, a gyroscope, or any other sensing device that can be used to detect the sensor data 118. The sensor data 118 describes characteristics of the agent, which may include a location, a biometric feature, or an activity of the agent. For example, the sensor data 118 detected by the sensors 115 may describe a temperature of the agent, a pulse of the agent, a calorie burn of the agent, a heart rate of the agent, a respiration activity of the agent, a physical activity of the agent, a sound emitted by the agent, a posture of the agent, a sleep activity of the agent, a GPS location of the agent, or a light surrounding the agent. In an embodiment, the agent device 103 includes multiple different types of sensors 115, and each of the sensors 115 detects a different type of sensor data 118.

The representative device 112 may be a user device, such as, for example, a wearable device, a mobile phone, a mobile tablet, an Internet of Things (IoT) device, a personal computer, or any device having access to memory and processing power. The representative device 112 comprises a graphical user interface 121, which can be used to display information related to the agent being monitored by the agent device 103 to a representative of the agent. The representative of the agent may be an individual who is interested in the safety and well-being of the agent being monitored. For example, the representative may be an owner of a pet being monitored using the agent device 103, a family member of an elderly relative being monitored using the agent device 103, an employee of a company requested to monitor the agent device 103, a researcher responsible for the living conditions of the agent, or a nurse/doctor who uses the collected health data to make assessment regarding the agent.

The cloud server 109 may be one or more devices or servers that provide services to the agent device 103 and the representative device 112 via the network 106. In some cases, the cloud server 109 may be a large scale data center located geographically remote from the agent device 103 and the representative device 112. The cloud server 109 may have far more powerful and extensive resources for computing processes and storing data than the agent device 103 and the representative device 112.

During operation, the agent device 103 intelligently determines whether sensor data 118 should be uploaded to the cloud server 109 or the representative device 112. To perform this intelligent determination, the agent device 103 uses a local learning model 122 stored at the agent device 103. In an embodiment, the local learning model 122 is a machine learning model including instructions or a file that is trained to recognize patterns from a sequence of data that is input into the local learning model 122. For example, the local learning model 122 may be based on a deep neural network, a recurrent neural network, a multi-task learning model, a transfer learning model, or any other type of neural network or machine learning model. In one embodiment, the local learning model 122 is computed using a long short-term memory recurrent neural network (RNN). Long short-term memory (LSTM) is an artificial recurrent neural network (RNN) architecture used in the field of deep learning. LSTM is also an effective manner by which to detect patterns in sequential data—LSTM can not only process single data points (e.g., images), but also entire sequences of data (e.g., speech or video).

Initially, the local learning model 122 at the agent device 103 is trained using training data that describes characteristics of agents similar to the agent wearing the agent device 103. For example, experts in the field may input collected data regarding similar agents into the local learning model 122 to train the local learning model 122. Further, the local learning model 122 that is initially loaded onto the agent device 103 may be additionally trained based on a set of demographics describing features of the agent that will be monitored by the agent device 103.

For example, when the agent device 103 is initially purchased to monitor a dog (e.g., agent), the set of demographics of the dog (e.g., species, gender, age, pre-existing conditions, etc.) may be provided to initially customize the local learning model 122 of the agent device 103. The agent device 103 may be pre-loaded to include the local learning model 122, which has already been trained based on training data describing similar dogs. The similar dogs may be the same species, be the same gender, have the same expected life-span, etc. The similar dogs may also have the same pre-existing conditions. In this way, the agent device 103 may be customized upon purchase by specifying a set of demographics that can be used to initially train the local learning model 122.

As the agent device 103 is used over time to monitor the agent, the local learning model 122 collects sensor data 118 from the agent, and uses the sensor data 118 to further train the local learning model 122. Feedback received from other devices, such as the representative device 112, may also be used to further train the local learning model 122. Generally, the more data that is fed into the local learning model 122, the more accurately the local learning model 122 predicts a condition, feature, or behavior of the agent over time. For example, the data that is fed into the local learning model 122 represents a history of behaviors of the agent or similar agents, some of which may be the sensor data 118. The agent device 103 consistently transmits the collected sensor data 118 to the cloud server 109 as the sensor data 118 is collected over time. At the cloud server, the cloud based learning model 131, which may include a feature embedding encoder/model, is trained based on sensor data 118 collected from multiple agent devices 103. The training at the cloud based learning model 131 helps fine tune the cloud based learning model 131 to generate more accurate predictions of the agent's condition or behavior. The fine-tuned cloud based learning model 131 is then sent back to the agent device 103, to update the local learning model 122 at the agent device 103, as will be further described below.

In an embodiment, the sensor data 118 is input into the local learning model 122 to generate, or compute, output data 125 that predicts a condition of the agent. The condition of the agent includes, but is not limited to, a physical or mental condition of the agent, a behavior of the agent, or a feature of the agent. The output data 125 may be a numerical value representing the predicted condition of the agent. As should be appreciated, the output data 125 may be in the form of an alphanumeric value, text, video, graphics, or any other form that represents the predicted condition. In addition, the output data 125 may be a combination of values over a period of time, and this combination can be obtained by summation, weighted averaged, conditioned decisions, etc.

When the agent device 103 includes multiple sensors 115, each of the sensors generates sensor data 118 based on the information detected by the sensors 115. The local learning model 122 receives the sensor data 118 from each of the sensors 115 and respectively generates output data 125 for each of the sensors 115.

For example, when the first sensor 115 is a thermometer, the first sensor 115 collects a temperature of the agent over an hour. After the hour, the agent device 103 obtains the collection of temperatures detected by the first sensor 115 over the hour, and provides the collection of temperatures to the local learning model 122 as an input. The local learning model 122 uses the collection of temperatures to determine a pattern of temperatures or determine changes within the pattern of temperatures that occurred within the hour of detection to predict a condition of the agent. For example, the local learning model 122 determines this pattern using the historical correlations that have been used to train the local learning model 122. The local learning model 122 predicts a condition of the agent (e.g., whether the agent is running a fever) based on the determined pattern of temperatures or changes within the pattern of temperatures that occurred within the hour of detection.

After identifying the behavior of the agent, the local learning model 122 computes the output data 125 by generating a value representing the predicted condition of the agent. For example, the agent device 103 normalizes the output data 125 computed for each of the sensors 115 by changing the values of the output data 125 into values within a common scale that can be analyzed together and compared against each other. This way, the agent device 103 can compare the normalized values of the output data 125 of different types of sensors 115 in the agent device 103. For example, a measured temperature of 101 degrees might translate to a value of 7 out of 10 on the common scale, and a measured heartrate of 75 beats per minute might translate to a value of 6 out of 10 on the common scale. Thus, the temperature reading has a higher importance or priority relative to the heartrate reading based on the common scale.

Instead of automatically forwarding the output data 125 representing the predicted condition of the agent to the cloud server 109 or the representative device 112, the agent device 103 first determines a power level of the battery 127. The power level of the battery 127 is a value or percentage representing how much energy is stored or remaining in the battery 127. The power level may be expressed as the amount of voltage that the battery 127 provides for a certain period of time. A higher a value of the power level, the more energy remaining in the battery 127.

After determining the power level of the battery 127, the agent device 103 determines whether uploading of the output data 125 is permitted at the determined power level of the battery 127. A determination of whether the output data 125 is permitted to be uploaded is based on an energy driven data profile for each of the sensors 115. In an embodiment, the energy driven data profile is stored at the agent device 103. An energy driven data profile includes one or more sensor conditions for a sensor 115. Each sensor condition for a specific sensor 115 specifies a pre-defined power level and a threshold value. The pre-defined power level specifies the power level upon which the sensor condition is triggered for the sensor 115. In an embodiment, the cutoff power level for a sensor 115 is one of the pre-defined power levels of the sensor 115. The threshold value is, for example, an integer or some other numerical value. The threshold value is compared with the output data 125 for that sensor 115 to determine whether the output data 125 is permitted to be uploaded. The threshold value of the sensor condition is associated with the predictive conditions, features, or behaviors of the agent that is indicated by the output data 125. When the output data 125 meets or exceeds the threshold value, then the predicted conditions, features, or behaviors indicated by the output data 125 is significant enough to notify the representative of the agent (e.g., upload the output data 125 to the cloud server 109 or representative device 112).

The agent device 103 determines whether the output data 125 for a sensor 115 meets the sensor condition by first determining whether a power level of the battery 127 meets (is less than or equal to) the pre-defined power level indicated by the sensor condition. If so, then the agent device 103 determines whether the output data 125 for the sensor 115 meets or exceeds (is less than or equal to, or is greater than or equal to) the threshold value indicated the sensor condition. If so, then the agent device 103 uploads the output data 125, or an indication of the output data 125, to the cloud server 109 or representative device 112.

Continuing with the example above, the agent device 103 stores the energy driven data profile for the first sensor 115 (e.g., the thermometer), which includes a first sensor condition. The first sensor condition indicates a pre-defined power level of 50 percent (%) and a threshold value of (5). In operation, the first sensor 115 detects sensor data 118 that is provided as input into the local learning model 122, and the local learning model 122 generates output data 125 for the first sensor 115 based on the sensor data 118. In this example, the local learning model 122 generates the output data 125 having the normalized value of 7.

First, the agent device 103 determines that the power level of the battery 127 meets the pre-defined power level specified by the sensor condition (e.g., whether the power level of the battery 127 has reached, is higher than (exceeds), or fallen below 50%). For example, if the pre-defined power level of the sensor condition is a pre-defined minimum power level, then the agent device 103 first determines whether the power level 127 exceeds the pre-defined power level. In another embodiment, if the pre-defined power level of the sensor condition is a maximum power level, then the agent device 103 determines whether the power level 127 has fallen below the pre-defined power level. The agent device 103 then compares the output data 125 of 7 to the threshold value of 5 to determine that the output data 125 for the sensor exceeds the threshold value of 5. To this end, the agent device 103 determines that the output data 125 for the first sensor 115 has met the sensor condition for the first sensor 115. The agent device 103 uploads the output data 125, or an indication of the output data 125, describing the predicted condition of the agent to the cloud server 109 or the representative device 112.

In contrast, the agent device 103 may determine that the power level of the battery 127 has not met the pre-defined power level specified by the sensor condition (e.g., the power level of the battery 127 has not reached, exceeded, or fallen below 50%). In this case, the agent device 103 determines that the output data 125 for the first sensor 115 did not meet the sensor condition for the first sensor 115. Similarly, when the power level of the battery 127 meets the pre-defined power level specified by the sensor condition but the output data 125 does not meet the threshold value of 5, then the agent device 103 determines that the output data 125 for the first sensor 115 did not meet the sensor condition for the first sensor 115. In both of these cases, the agent device 103 locally stores the output data 125 in a memory of the agent device 103, instead of uploading the output data 125 to the cloud server 109 or the representative device 112.

In an embodiment, different sensors 115 of the agent device 103 have different sensor conditions, which are used differently to prevent unnecessarily uploading insignificant behavioral changes of the agent as the battery life of the agent device 103 decreases. Meanwhile, the agent device 103 retains the ability to upload information signaling significant dangers or behavioral changes of the agent to the cloud server 109 or the representative device 112 even as the battery life of the agent device 103 decreases. Therefore, the embodiments disclosed herein increase the battery life of the agent device 103 by intelligently decreasing the amount of resources consumed by the agent device 103 over time.

In an embodiment, the cloud server 109 is also configured to maintain a cloud based learning model 131, which is similar to the local learning model 122. However, the cloud based learning model 131 is trained using large sets of training data 134. As used herein, large sets of training data 134 means training data that not only includes the sensor data 118 and the output data 125 from the agent device 103 monitoring the agent, but also sensor data and output data from numerous other agent devices 103 monitoring similar agents. Experts may also input training data 134 describing conditions, features, and behaviors that are applicable to the agent. In some embodiments, the cloud server 109 maintains a different cloud based learning model 131 for different agents beings monitored using different agent devices 103.

The cloud server 109 receives and stores much more information in the training data 134 than the agent device 103 is capable of receiving and storing. The cloud server 109 also has the processing power and resources to label large amounts of incoming data (sensor data 118, output data 125, training data 134, and other data), which can be used to further the cloud based learning model 131 for an agent. The cloud server 109 maintains updates to the local learning model 122 in the cloud based learning model 131, and transmits the updates to the local learning model 122 to the agent device 103 via network 106. In this way, the agent device 103 does not have to receive and maintain large amounts of data to further train the local learning model 122. Instead, the agent device 103 relies on the cloud server 109 to maintain and update the cloud based learning model 131 based on the incoming data, and then forwards the updates to the agent device 103. In this way, the local learning model 122 on the agent device 103 is periodically updated, on a scheduled or as needed basis, to more accurately predict conditions of the agent over time.

Therefore, the embodiments disclosed herein provide a customized agent device 103 for different agents, thereby enabling a more accurate prediction of the behavior of the agent over time. By offloading the more resource intensive computations to the cloud server 109, the battery life of the agent device 103 can be significantly increased, while increasing the accuracy of predicting the conditions of the agent.

Figure 2:
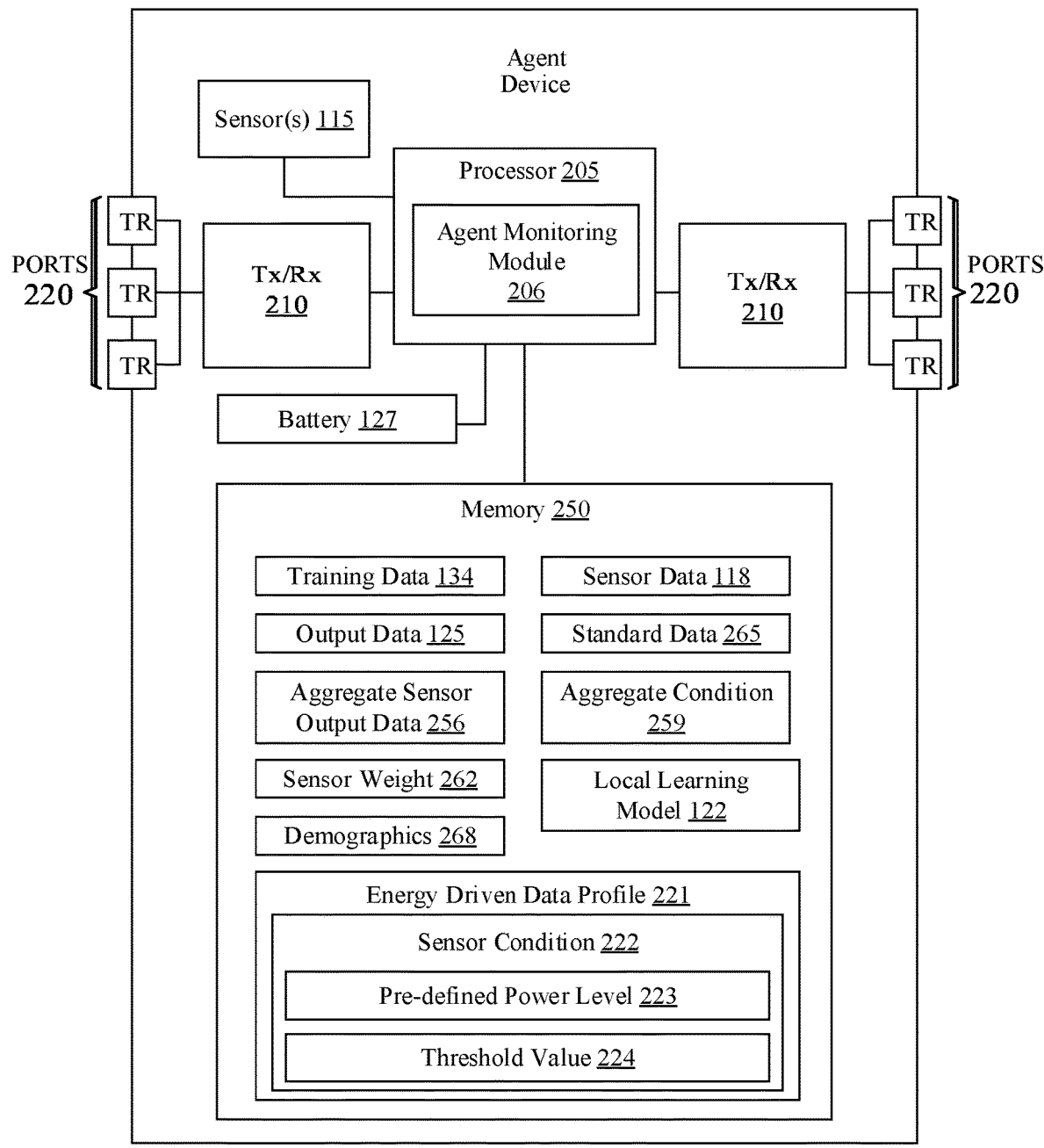
FIG. 2 is a diagram illustrating the agent device of the agent monitoring system according to various embodiments of the disclosure.

FIG. 2 is a diagram of an embodiment of the agent device 103 according to various embodiments of the disclosure. The agent device 103 may be configured to implement and/or support the power efficient agent monitoring mechanisms and schemes described herein. The agent device 103 may be implemented in a single node or the functionality of the computing agent 103 may be implemented in a plurality of nodes. One skilled in the art will recognize that the term agent device encompasses a broad range of devices of which agent device 103 is merely an example. For example, the agent device 103 can be a general purpose computer, a mobile device, a tablet device, a wearable device, or any other type of user equipment. The agent device 103 shown in FIG. 2 is included for purposes of clarity of discussion, but is in no way meant to limit the application of the present disclosure to a particular computing device embodiment or class of computing device embodiments.

At least some of the features/methods described in the disclosure are implemented in a computing apparatus or component such as the agent device 103. For instance, the features/methods in the disclosure may be implemented using hardware, firmware, and/or software installed to execute on hardware. As shown in FIG. 2, the agent device 103 comprises one or more sensors 115, which may be a GPS locator, an altimeter, a BLUETOOTH device, a microphone, a thermometer, a pulse oximeter, a heart rate monitor, a camera, an accelerometer, a gyroscope, or any other sensing device. The agent device 103 also comprises a battery 127 configured to provide power to the agent device 103. The agent device 103 also comprises transceivers (Tx/Rx) 210, which may be transmitters, receivers, or combinations thereof. The Tx/Rx 210 is coupled to a plurality of ports 220 for transmitting and/or receiving packets from other nodes.

A processor 205 is coupled to each Tx/Rx 210. The processor 205 may comprise one or more multi-core processors and/or memory devices 250, which may function as data stores, buffers, etc. The processor 205 may be implemented as a general processor or by one or field programmable gate arrays (FGPAs), application specific integrated circuits (ASICs), and/or digital signal processors (DSPs).

In one embodiment, the processor 205 comprises internal logic circuits to implement the agent monitoring module 206, and may comprise internal logic circuits to implement the functional steps in processes 300 and 400 and methods 500, 600, and 100, as discussed more fully below, and/or any other flowcharts, schemes, and methods discussed herein. As such, the inclusion of the agent monitoring module 206 and associated methods and systems provide improvements to the functionality of the agent device 103. In an alternative embodiment, the agent monitoring module 206 may be implemented as instructions stored in the memory device 250, which may be executed by the processor 205 to perform the operations of the agent monitoring module 206. Furthermore, the agent monitoring module 206 can optionally be omitted from the agent device 103.

The memory device 250 may comprise a cache for temporarily storing content, e.g., a random-access memory (RAM). Additionally, the memory device 250 may comprise a long-term storage for storing content relatively longer, for example, a read-only memory (ROM). For instance, the cache and the long-term storage may include dynamic RAMs (DRAMs), solid-state drives (SSDs), hard disks, or combinations thereof.

The memory device 250 may be configured to store the training data 134, the sensor data 118, the output data 125, the energy driven data profile 221, an aggregate sensor output data 256, an aggregate condition 259, a sensor weight 262, standard data 265, demographics 268, and the local learning model 122.

The sensor data 118 is the data obtained (e.g., detected) from the sensors 115 during operation of the agent device 103. The local learning model 122 is the machine language learning model implemented at the agent device 103. The output data 125 is the data used to indicate a predicted condition of the agent wearing the agent device 103. The local learning model 122 uses the sensor data 118 as an input to generate the output data 125 based on the training data 134.

The training data 134 is data used to build the cloud based learning model 131 and the local learning model 122. The training data 134 may include sensor data 118, output data 125, and other data received from one or more agent devices 103. The training data 134 may also include test data, which is data used to validate that the cloud based learning model 131 and the local learning model 122.

The energy driven data profile 221 may be specified for each of the sensors 115 in the agent device 103. In an embodiment, the energy driven data profile 221 is a lookup table with mappings indicating the sensor conditions 222 for each of the sensors 115. A mapping may indicate an identifier of the sensor 115 and one or more sensor conditions 222 for that sensor 115. The sensor condition 222 defines a pre-defined power level 223 and a threshold value 224. The sensor condition 222 indicates whether to upload the output data 125 based on whether a power level 310 (show in FIG. 3) of the battery 127 meets the pre-defined power level 223 and based on whether the output data 125 of a sensor 115 meets the threshold value 224.

The aggregate sensor output data 256 is a value indicating an overall behavior of the agent based on an aggregation formula that considers the sensor data 118 and output data 125 of all sensors 115 on the agent device 103. The aggregation formula used to calculate the aggregate sensor output data 256 is based on a sensor weight 262 for each of the sensors 115. The sensor weight 262 indicates a priority or significance of the respective sensor 115.

The aggregate condition 259 defines at least one of a pre-defined power level 223 and a pre-defined aggregate threshold value. The aggregate condition 259 indicates whether to upload all the determined output data 125 based on whether a power level 310 of the battery 127 meets the pre-defined power level 223 and based on whether the aggregate sensor output data 256 of all the sensors 115 meets the pre-defined aggregate threshold value.

The standard data 265 indicates a baseline normal behavior of the agent. The local learning model 122 (or the cloud based learning model 131) may determine the standard data 265 based on collected sensor data 118 and output data 125 from the agent device 103. The standard data 265 may be a normalized value, and each sensor 115 may be associated with standard data 265 for the respective sensor 115. The demographics 268 describe features of the agent wearing the agent device 103, such as, for example, a species, gender, age range, pre-existing conditions, or any other feature of the agent being monitored by the agent device 103.

It is understood that by programming and/or loading executable instructions onto the agent device 103, at least one of the processor 205 and/or memory device 250 are changed, transforming the agent device 103 in part into a particular machine or apparatus, e.g., a multi-core forwarding architecture, having the novel functionality taught by the present disclosure. It is fundamental to the electrical engineering and software engineering arts that functionality that can be implemented by loading executable software into a computer can be converted to a hardware implementation by well-known design rules. Decisions between implementing a concept in software versus hardware typically hinge on considerations of stability of the design and numbers of units to be produced rather than any issues involved in translating from the software domain to the hardware domain. Generally, a design that is still subject to frequent change may be preferred to be implemented in software, because re-spinning a hardware implementation is more expensive than re-spinning a software design. Generally, a design that is stable and that will be produced in large volume may be preferred to be implemented in hardware, for example in an ASIC, because for large production runs the hardware implementation may be less expensive than the software implementation. Often a design may be developed and tested in a software form and later transformed, by well-known design rules, to an equivalent hardware implementation in an ASIC that hardwires the instructions of the software. In the same manner as a machine controlled by a new ASIC is a particular machine or apparatus, likewise a computer that has been programmed and/or loaded with executable instructions (e.g., a computer program product stored in a non-transitory medium/memory) may be viewed as a particular machine or apparatus.

Figure 3:
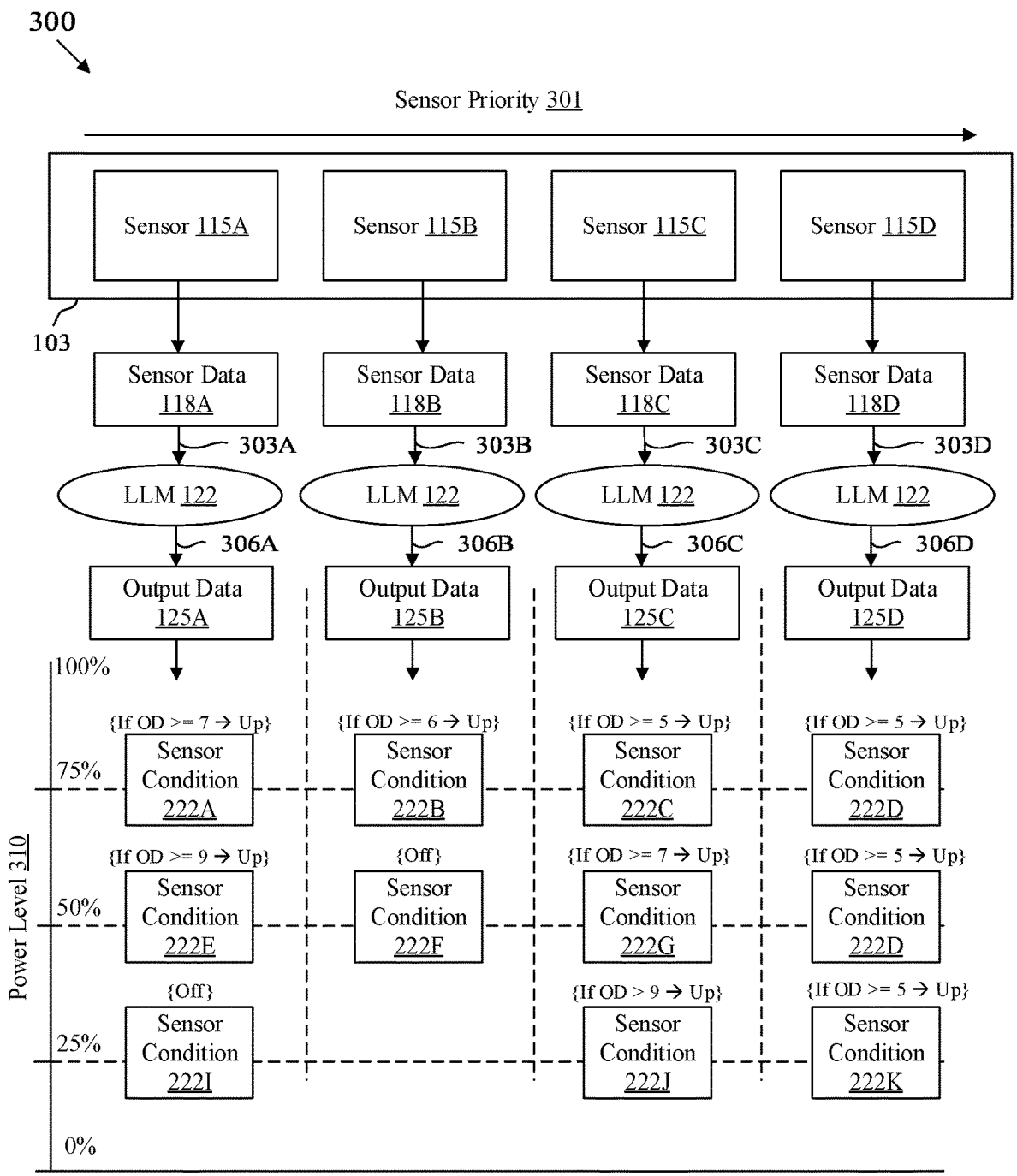
FIG. 3 is a diagram illustrating a process performed for each sensor on the agent device to implement power efficient monitoring according to various embodiments of the disclosure.

FIG. 3 is a diagram illustrating a process 300 performed for each sensor 115 on the agent device 103 to implement power efficient monitoring according to various embodiments of the disclosure. In the example shown in FIG. 3, the agent device 103 includes four sensors 115A-D. Each of the sensors 115A-D obtains (e.g., detects) different types of sensor data 118A-D, respectively, for a pre-defined period of time.

For example, sensor 115A may be a microphone, sensor 115B may be a heart rate monitor, sensor 115C may be a thermometer, and sensor 115D may be a GPS locator (e.g., a GPS transceiver). In this example, the sensor data 118A-D may be collected by each of the sensors 115A-D for a period of one hour. The sensor 115A (e.g., microphone) obtains sensor data 118A describing audio signals received by, at, and around the agent during the hour. The sensor 115B (e.g., heart rate monitor) obtains sensor data 118B describing the various heart rates of the agent during the hour. The sensor 115C (e.g., thermometer) obtains sensor data 118C describing the various temperatures of the agent during the hour. The sensor 115D (e.g., GPS locator) obtains sensor data 118D describing the different locations at which the agent was located during the hour.

The sensors 115A-D are shown in FIG. 3 in an order of increasing sensor priority 301. That is, sensor 115A has the lowest priority, while sensor 115D has the highest priority. In an embodiment, the sensor priority 301 is a value indicating a priority of the sensor 115A-D, which may be pre-configured by an operator of the agent device 103. The priority of the sensor 115A-D may be based on a property of the agent and an energy consumption of the sensors 115A-D. The property of the agent, for example, indicates whether the agent is an animal, a robot, or a human being. If the agent is a human being, the property may indicate whether the agent is an infant or an elderly person. If the agent is a human being, sensors 115A-D responsible for collecting an agent's vital signs, such as the heart rate and respiration, be assigned the highest priority. However, if the agent is a robot, the sensors 115A-D responsible for collecting vital signs may not be as significant, and thus, may be assigned a lower priority. In addition, audio and video camera sensors 115A-D consume the most power during operation and uploading, and thus, may be assigned a lower priority to increase the battery life of the agent device 103. In an embodiment, the priority for each of the sensors 115A-D is pre-configured for each agent based on the properties of the agent and the energy consumption of each of the sensors 115A-D. In an embodiment, the local learning model 122 and/or the cloud based learning model 131 may adjust the priority for a sensor 115A-D as the models are better trained. In some embodiments, the sensor priority is also presented in cutoff power level or pre-defined power level. For example, a first sensor 118A that has pre-defined power level of 25% has a higher priority than a second sensor 118 that has pre-defined power level of 50%. Because, when the power level reaches 30%, the first sensor 118 is still working, while the second sensor 118 is turned off.

The agent device 103 provides the sensor data 118A-D as input 303A-D of the local learning model 122 (shown as "LLM 122" in FIG. 3), respectively. As shown by FIG. 3, the local learning model 122 receives the sensor data 118A as input 303A, receives sensor data 118B as input 303B, receives sensor data 118C as input 303C, and receives sensor data 118D as input 303D.

The local learning model 122 uses the received sensor data 118A-D to generate output data 125A-D. For example, the local learning model 122 identifies a pattern in the audio signals in the sensor data 118A to predict a condition of the agent. As described above, the predicted condition may be a mental condition, physical condition, feature, attribute, or behavior of the agent. The local learning model 122 generates the output data 125A indicating the predicted condition of the agent. In addition, the local learning model 122 identifies similar patterns, changes, or irregularities in the sensor data 118B-D to generate output data 125B-D. For example, the local learning model 122 identifies an irregularity in the heart rate of the agent based on the sensor data 118B. The local learning model 122 generates the output data 125B indicating a prediction that the agent is experiencing a heart issue based on the heart rate irregularity. Similarly, the local learning model 122 identifies a change in the temperature of the agent based on the sensor data 118B for an extended period of time. The local learning model 122 generates the output data 125C indicating that the agent is ill based on the temperature change. Finally, the local learning model 122 identifies a pattern in a location change of the agent based on the sensor data 118D. The local learning model 122 generates the output data 125D indicating the location change of the agent. The output data 125A-D is the output 306A-D of the local learning model 122, respectively.

As described above, the output data 125A-D may be a numeric value that has been normalized such that the output data 125A-D can be compared against output data 125A-D of the different types of sensors 115A-D. Instead of automatically uploading the output data 125A-D to the cloud server 109 (see FIG. 1) or the representative device 112 (see FIG. 1), the agent device 103 first uses the energy driven data profile 221 (see FIG. 2) for each of the sensors 115A-D to determine whether to upload the output data 125A-D. The energy driven data profile 221 for a sensor 115 indicates sensor conditions 222 dictating whether output data 125A-D should be uploaded at different power levels 310 of the battery 127 (see FIG. 1).

First, the agent device 103 determines a power level 310 of the battery 127 of the agent device 103. In an embodiment, the agent device 103 is configured to upload the output data 125A-D, or an indication of the output data 125, differently based on the power level 310 of the battery 127 and the sensor conditions 222 for each of the sensors 115A-D.

In some cases, the sensor conditions 222 for each of the sensors 115A-D also define when to power off that particular sensor 115A-D. In an embodiment, the agent device 103 uses a parameter (a) indicating whether data of a sensor 115A-D can be processed based on the power level 310 of the battery 127 at time t, where a=1 means a sensor can be processed and a=0 means a sensor cannot be processed. Assuming the agent device 103 has (m) power levels 310, and the higher the power level 310, the more power that is left in the battery 127. Suppose each of the sensors 115A-D is associated with a preset cutoff level ($b_i$), in which i represents a sensor 115A-D. The preset cutoff level ($b_i$) is a value between $\{1, \ldots, m\}$. A cutoff level $b_i$ means sensor i won't be processed if the device power is lower than $b_i$. Thus, the higher the cutoff level, the less priority the sensor has. In this case, the parameter (a) for sensor i at time t is defined by the following equation (1):

$$a_i^t = H(b_t - b_i) = \begin{cases} 1, & \text{if } b_i \le b_t \\ 0, & \text{if } b_i > b_t \end{cases} \quad (1)$$

In equation (1), H is a Heaviside function (a.k.a., a Heaviside step function or a unit step function), $b_t$ is the power level 310 at time t, and a may be normalized based on the sensors 115A-D of the agent device 103. A Heaviside function is a discontinuous function whose value is zero for negative arguments and one for non-negative arguments. For example, a Heaviside function may represent a signal that switches on at a specified time and stays switched on indefinitely. In equation (1), the sensor 115A-D is only permitted to work when the power level 310 exceeds the cutoff power level for the sensor 115A-D. The agent device 103 uses equation (1) to determine whether or not to power off a sensor 115A-D at a particular power level 310 of the battery 127. If the sensor 115A-D does not need to be powered off, then the agent device 103 uses the sensor condition 222 to determine whether to upload the output data 125.

As shown by FIG. 3, when the power level 310 of the battery 127 reaches a pre-defined power level 223 of 75%, each of the sensors 115A-D has a different sensor condition 222A-D. For sensor 115A, sensor condition 222A indicates that, when the power level 310 of the battery 127 reaches a pre-defined power level 223 of 75%, only output data 125A that meets a threshold value 224 may be uploaded. The threshold value 224 for the sensor condition 222A may be 7. In this case, if the output data 125A is less than 7, then the agent device 103 locally stores the output data 125A instead of uploading the output data 125A to the cloud server 109 or the representative device 112. In contrast, if the output data 125A is greater than or equal to 7, then the agent device 103 is triggered to upload the output data 125A to the cloud server 109 or the representative device 112.

For sensor 115B, sensor condition 222B indicates that, when the power level 310 of the battery 127 reaches a pre-defined power level 223 of 75%, only output data 125B that meets a threshold value 224 may be uploaded. The threshold value 224 for the sensor condition 222B may be 6. In this case, if the output data 125B is less than 6, then the agent device 103 locally stores the output data 125B instead of uploading the output data 125B. In contrast, if the output data 125B is greater than or equal to 6, then the agent device 103 is triggered to upload the output data 125B.

For sensor 115C, sensor condition 222C indicates that, when the power level 310 of the battery 127 reaches a pre-defined power level 223 of 75%, only output data 125C that meets a threshold value 224 may be uploaded. The threshold value for the sensor condition 222C may be 5. In this case, if the output data 125C is less than 5, then the agent device 103 locally stores the output data 125C instead of uploading the output data 125C. In contrast, if the output data 125C is greater than or equal to 5, then the agent device 103 is triggered to upload the output data 125C.

For sensor 115D, sensor condition 222D indicates that, when the power level 310 of the battery 127 reaches a pre-defined power level 223 of 75%, only output data 125D that meets a threshold value 224 may be uploaded. The threshold value 224 for the sensor condition 222D may be 5. In this case, if the output data 125D is less than 5, then the agent device 103 locally stores the output data 125D instead of uploading the output data 125D. In contrast, if the output data 125D is greater than or equal to 5, then the agent device 103 is triggered to upload the output data 125D.

In the example shown in FIG. 3, the threshold value 224 for each of the sensor conditions 222A-D is a numerical value, in which the higher the threshold value 224, the stricter the sensor condition 222A-D. The stricter the sensor condition 222A-D and the higher the threshold value 224, the less data that is actually uploaded from the agent device 103.

At a specific power level 310, the sensors 115A-D that are not powered off can be evaluated based on a sensor priority. In addition, sensors 115A-D that have a higher sensor priority 301 also have a less strict sensor condition 222A-D (e.g., lower threshold values 224). This enables more data to be uploaded from the higher priority sensors 115C-D than from the lower priority sensors 115A-B.

Each of the sensors 115A-D may also have different sensor conditions 222A-K at various different power levels 310. One or more these sensors 115A-D have many stricter sensor conditions 222A-K (e.g., higher threshold values 224) as the power level 310 of the battery 127 decreases. As shown by FIG. 3, when the power level 310 of the battery 127 reaches a pre-defined power level 223 of 50%, each of the sensors 115A-D has a different sensor condition 222A-D.

For sensor 115A, sensor condition 222E indicates that, when the power level 310 of the battery 127 reaches a pre-defined power level 223 of 50%, only output data 125A that meets a threshold value 224 may be uploaded. The threshold value 224 for the sensor condition 222E may be 9, which is stricter than the threshold value 224 for the sensor condition 222A. In this case, if the output data 125A is less than 9, then the agent device 103 locally stores the output data 125A instead of uploading the output data 125A to the cloud server 109 or the representative device 112. In contrast, if the output data 125A is greater than or equal to 9, then the agent device 103 is triggered to upload the output data 125A to the cloud server 109 or the representative device 112.

For sensor 115B, sensor condition 222F indicates that, when the power level 310 of the battery 127 reaches a pre-defined power level 223 of 50%, the sensor 115B is turned off. In this way, when the power level 310 of the battery 127 meets 50% (reaches or is lower than 50%), the sensor 115B is turned off to further preserve the battery life of the battery 127.

For sensor 115C, sensor condition 222G indicates that, when the power level 310 of the battery 127 reaches a pre-defined power level 223 of 50%, only output data 125C that meets a threshold value 224 may be uploaded. The threshold value 224 for the sensor condition 222G may be 7, which is stricter than the threshold value 224 for the sensor condition 222C. In this case, if the output data 125C is less than 7, then the agent device 103 locally stores the output data 125C instead of uploading the output data 125C. In contrast, if the output data 125C is greater than or equal to 7, then the agent device 103 is triggered to upload the output data 125C.

For sensor 115D, when the power level 310 of the battery 127 reaches a pre-defined power level 223 of 50%, the sensor condition 222D remains the same. Since the sensor priority 301 for sensor 115D is the highest, then the sensor condition 222D, or the threshold value 224 of the sensor condition 222D, for the highest sensor priority 301 sensor 115D remains the same. This way, the output data 125D for the sensor 115D has the highest sensor priority in action, such as in uploading or decision making. The sensor priority may only apply to the sensors 115A-D that are not powered off.

When the power level 310 of the battery reaches a pre-defined power level 223 of 25%, each of the sensors 115A-D may yet again have a different sensor condition 222A-D. For sensor 115A, sensor condition 222I indicates that, when the power level 310 of the battery 127 reaches a pre-defined power level 223 of 25%, the sensor 115A is turned off.

For sensor 115C, sensor condition 222J indicates that, when the power level 310 of the battery 127 reaches a pre-defined power level 223 of 25%, only output data 125C that meets a threshold value 224 may be uploaded. The threshold value 224 for the sensor condition 222J may be 9, which is stricter than the threshold value 224 for the sensor condition 222C and 222G. In this case, if the output data 125C is less than 9, then the agent device 103 locally stores the output data 125C instead of uploading the output data 125C to the cloud server 109 or the representative device 112. In contrast, if the output data 125C is greater than or equal to 9, then the agent device 103 is triggered to upload the output data 125C to the cloud server 109 or the representative device 112.

Again, the sensor condition 222D remains the same for sensor 115D because of the sensor priority 301 of the sensor 115D. This way, the output data 125D for the sensor 115D is uploaded. The output data 125D, signaling a GPS location pattern of the agent, may be transmitted to the cloud server 109 or the representative device 112 as long as the current power level 310 is higher than the cutoff power level.

In this example, the agent device 103 compares the output data 125A-D with the threshold value 224 for each of the sensor conditions 222A-K to determine whether to upload the output data 125. In another embodiment, the agent device 103 may first determine a difference between the output data 125A-D and the standard data 265 for each sensor 115A-D. The standard data 265 for the sensor 115A-D represents a baseline normal behavior of the agent, which may be determined by the local learning model 122 or the cloud based learning model 131. Alternatively, the standard data 265 may be pre-configured by an operator of the agent device 103. The standard data 265 may be a normalized value that can be compared with the output data 125A-D, and each sensor 115A-D may be associated with standard data 265 for the respective sensor 115A-D.

The computed difference may be compared with the threshold value 224 for each of the sensor conditions 222A-K to determine whether to upload the output data 125. For example, agent device 103 may first determine a difference between the standard data 265 corresponding to sensor 115A, which may indicate a standard noise level of the agent. Then, the agent device 103 computes a difference between the output data 125A-D and the standard data 265, which indicates a deviation from the standard features or behaviors of the agent 103. The agent device 103 then compares the difference to the threshold value 224 of 7 to determine whether the output data 125A-D is significant enough to notify the representative. If so, the agent device 103 uploads the output data 125A-D, or an indication of the output data 125A-D, to the cloud server 109 or the representative device 112.

The output data 125A-D may be uploaded as simply the value of the output data 125A-D. Alternatively, the output data 125A-D may be uploaded in another form (e.g., textually or visually) that enables a representative of the agent to easily determine the predicted condition of the agent represented by the output data 125A-D.

The embodiments disclosed herein enable the agent device 103 to control the amount of data that is uploaded or transmitted to the cloud server 109 or the representative device 112, thereby consuming resources at the agent device 103 and draining the battery 127. The agent device 103 controls the amount of data uploaded based on the sensor condition 222A-K, which indicates a pre-defined power level 223 and a threshold value 224. The agent device 103 compares the power level 310 of the battery 127 with the pre-defined power level 223, and then compares the output data 125A-D with the threshold value 224 to determine whether the output data 125A-D should be uploaded.

The example shown in FIG. 3 illustrates that higher threshold values are associated with stricter sensor conditions 222A-K, and lower threshold values are associated with less strict sensor conditions 222A-K. However, it should be appreciated that the threshold values for the sensor conditions 222A-K may be defined in any manner. For example, lower threshold values can be associated with stricter sensor conditions 222A-K, and higher threshold values can be associated with less strict sensor conditions 222A-K. While only four power levels 310 are shown in FIG. 3 as being associated with the different pre-defined power levels 233, it should be appreciated that any number of power levels 310 may be associated with different pre-defined power levels 233.

Figure 4:
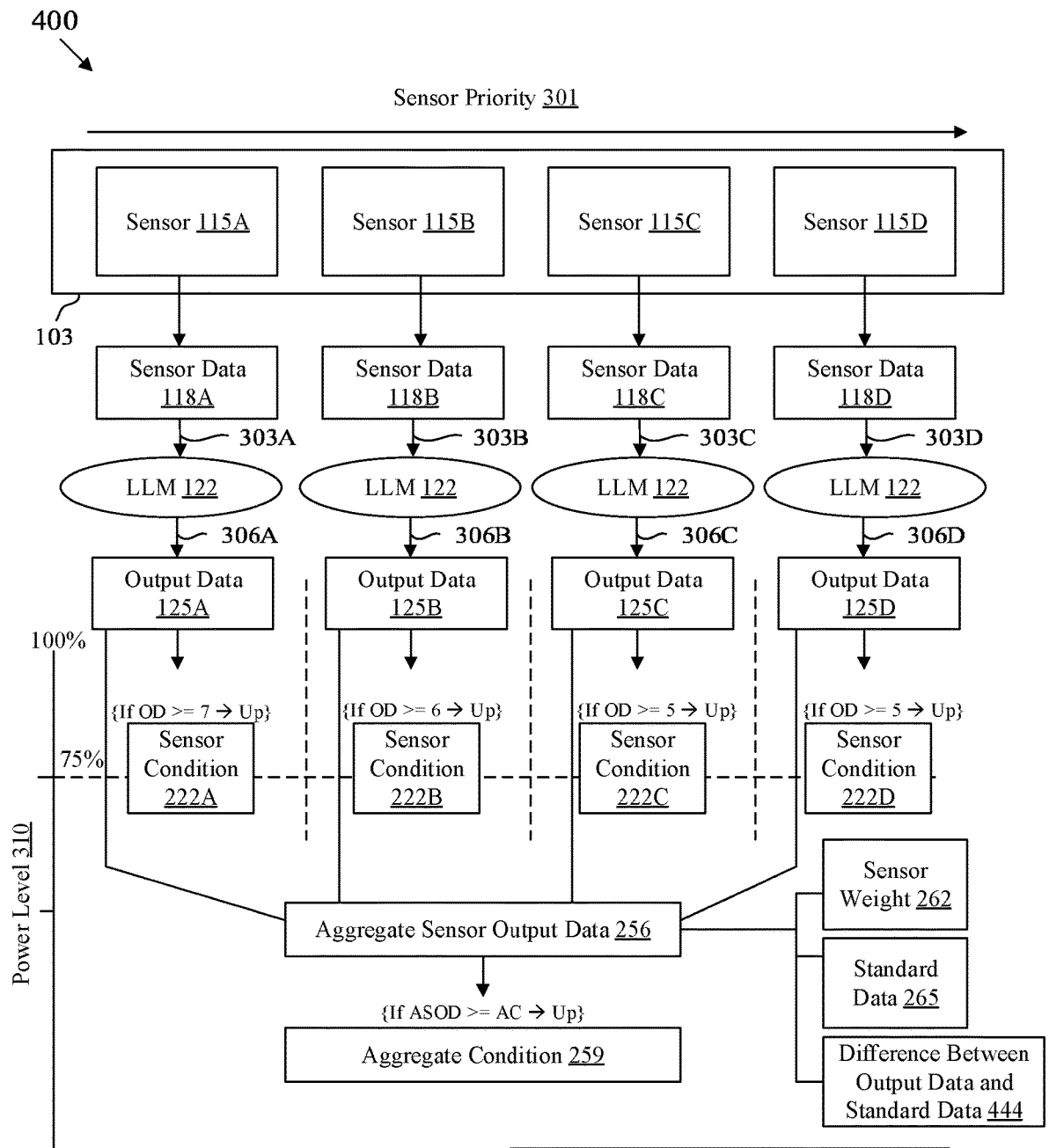
FIG. 4 is a diagram illustrating another process performed for each sensor on the agent device to implement power efficient monitoring according to various embodiments of the disclosure.

FIG. 4 is a diagram illustrating another process 400 performed for each sensor 115A-D on the agent device 103 to implement power efficient monitoring according to various embodiments of the disclosure. Process 400 of FIG. 4 is similar to process 300 of FIG. 3, except that, in process 400, the agent device 103 computes an aggregate sensor output data 256. The agent device 103 compares the aggregate sensor output data 256 with an aggregate condition 259 to determine whether to upload the output data 125A-D. Process 400 and process 300 can be in the same device.

In FIG. 4, the agent device 103 includes four sensors 115A-D, which each obtain (e.g., detect) sensor data 118A-D. The agent device 103 provides the sensor data 118A-D as input 303A-D to the local learning model 122 (shown as "LLM 122" in FIG. 4), respectively. The local learning model 122 uses the received sensor data 118A-D and the trained machine learning model to generate output data 125A-D. The output data 125A-D is the output 306A-D of the local learning model 122, respectively.

As shown by FIG. 4, when the power level 310 of the battery 127 reaches a pre-defined power level 223 of 75%, each of the sensors 115A-D has a different sensor condition 222A-D. The sensor conditions 222A-D of FIG. 4 are the same as the sensor conditions 222A-D of FIG. 3.

For sensor 115A, sensor condition 222A indicates that, when the power level 310 of the battery 127 reaches a pre-defined power level 223 of 75%, only output data 125A that meets a threshold value 224 may be uploaded. In the example shown in FIG. 4, the output data 125A does not meet the threshold value 224 of the sensor condition 222A. That is, the output data 125A is less than 7.

For sensor 115B, sensor condition 222B indicates that, when the power level 310 of the battery 127 reaches a pre-defined power level 223 of 75%, only output data 125B that meets a threshold value 224 may be uploaded. In the example shown in FIG. 4, the output data 125B does not meet the threshold value 224 of the sensor condition 222B. That is, the output data 125B is less than 5.

For sensor 115C, sensor condition 222C indicates that, when the power level 310 of the battery 127 reaches a pre-defined power level 223 of 75%, only output data 125C that meets a threshold value 224 may be uploaded. In the example shown in FIG. 4, the output data 125C does not meet the threshold value 224 of the sensor condition 222C. That is, the output data 125C is less than 5.

For sensor 115D, sensor condition 222D indicates that, when the power level 310 of the battery 127 reaches a pre-defined power level 223 of 75%, only output data 125D that meets a threshold value 224 may be uploaded. In the example shown in FIG. 4, the output data 125D does not meet the threshold value 224 of the sensor condition 222D. That is, the output data 125D is less than 5.

In this case, none of the sensor conditions 222A-D for any of the sensors 115A-D have been met. The agent device 103 locally stores the output data 125A-D instead of uploading the output data 125A-D to the cloud server 109 or the representative device 112.

In an embodiment, the agent device 103 may be configured to determine the aggregate sensor output data 256, which represents an overall condition, feature, or behavioral characteristic of the agent using the output data 125A-D from all of the sensors 115A-D, instead of just a condition determined using the output data 125A-D of a single sensor 115. The aggregate sensor output data 256 (asod) is computed as an aggregation of the output data 125A-D from all of the sensors 115A-D based on the following aggregation formula:

$$\text{asod} = \sum_{i=1}^{n} w_i \alpha_i L_i \qquad (2)$$

In equation 2, i represents a sensor 115A-D, $w_i$ is a sensor weight 262 of the sensor 115, α represents a value of the sensor data 118 after being filtered, normalized, and interpolated, and $L_i$ is a difference 444 between the standard data 265 for the sensor 115A-D and the output data 125A-D for the sensor 115A-D. The standard data 265 for the sensor 115A-D represents a baseline normal behavior of the agent. The aggregate sensor output data 256 is normalized such that the aggregate sensor output data 256 can be compared to the pre-defined aggregate threshold value of the aggregate condition 259.

In an embodiment, the agent device 103 compares the aggregate sensor output data 256 with the aggregate condition 259. The aggregate condition 259 defines at least one of a pre-defined power level 223 and a pre-defined aggregate threshold value that should be met for the output data 125A-D or the aggregate sensor output data 256 to be uploaded.

In this case, when the power level 310 of the agent device 103 meets (e.g., has reached, exceeded, or fallen below) the pre-defined power level 223 of 75% and none of the output data 125A-D has met the sensor conditions 222, the agent device 103 determines whether the aggregate sensor output data 256 has met the aggregate condition 259. When the aggregate sensor output data 256 is less than the pre-defined aggregate threshold value of the aggregate condition 259, then the agent device 103 determines that the aggregate sensor output data 256 has not met the aggregate condition 259. In this case, the agent device 103 locally stores the aggregate sensor output data 256 and/or the output data 125A-D.

Alternatively, when the aggregate sensor output data 256 is greater than or equal to the pre-defined aggregate threshold value of the aggregate condition 259, the agent device 103 determines that the aggregate sensor output data 256 has met the aggregate condition 259. In this case, the agent device 103 uploads the output data 125A-D or the aggregate sensor output data 256 to the cloud server 109 or the representative device 112.

The output data 125A-D or the aggregate sensor output data 256 may be uploaded as simply the value of the output data 125A-D or the aggregate sensor output data 256. Alternatively, the aggregate sensor output data 256 may be uploaded in another form (e.g., textually or visually) that enables a representative of the agent to easily determine the predicted condition of the agent represented by the output data 125A-D or the aggregate sensor output data 256.

Figure 5:
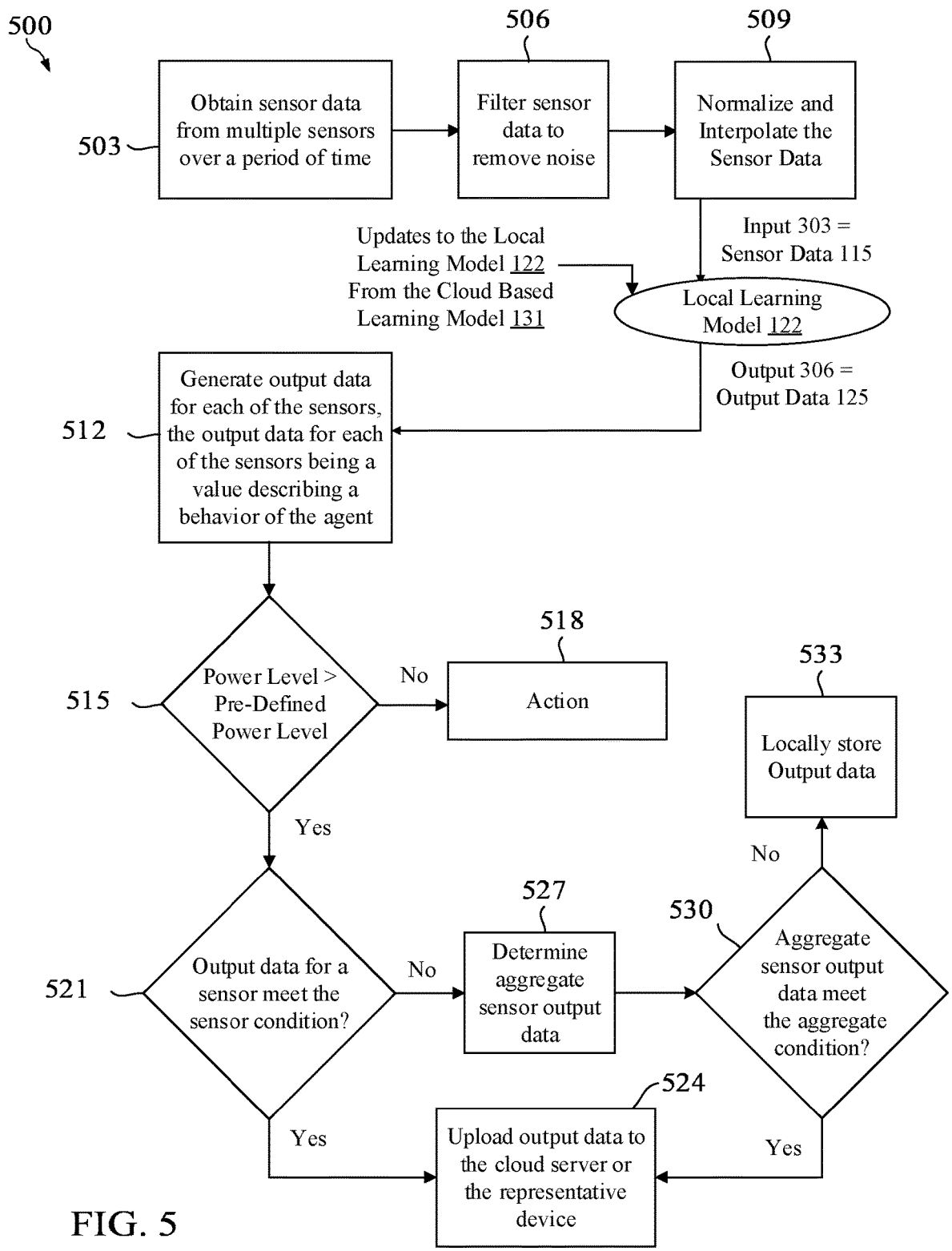
FIG. 5 is flowchart illustrating a method for power efficient monitoring performed by the agent device of the agent monitoring system according to various embodiments of the disclosure.

FIG. 5 is a flowchart illustrating a method 500 for power efficient monitoring according to various embodiments of the disclosure. The agent device 103 performs the method 500 upon activating the sensors 115A-D (hereinafter referred to as "sensors 115") on the agent device 103. Method 500 illustrates how the agent device 103 operates to perform the processes 300 and 400 of FIGS. 3 and 4. In an embodiment, the agent device 103 has been pre-loaded with initial data and information, as described herein, prior to activating the sensors 115.

At step 503, the sensors 115 obtain sensor data 118 over a period of time. For example, a sensor 115 may be a microphone, and the sensor 115 obtains audio signals over a period of time. The audio signals include the sounds made by the agent and environmental sounds emitting from the environment surrounding the agent.

At step 506, the agent device 103 filters the sensor data 118 to remove noise unrelated to the agent. For example, the agent device 103 removes noise from the audio signals, such as the sound from cars driving by the agent, or people having a conversation around the agent.

At step 509, the agent device 103 normalizes and interpolates the sensor data 118 to arrange the sensor data 118 in a manner such that the sensor data 118 can be used by the local learning model 122 to generate output data 125A-D (hereinafter referred to as "output data 125"). After normalizing and interpolating the sensor data 118, the agent device 103 provides the sensor data 118 to the local learning model 122 as an input 303. In some embodiments, the agent device 103 receives updates to the local learning model 122 from the cloud based learning model 131.

At step 512, the local learning model 122 generates output data 125 for each of the sensors 115. The output data 125 is a normalized value describing a predicted condition of the agent wearing the agent device 103. Continuing with the example above, the local learning model 122 uses the sensor data 118 to generate output data 125 indicating that the agent was yelping and whimpering for at least 20 minutes of the period of time during which the sensor data 118 was collected. The learning model 122 generates a normalized value representing that the agent was yelping and whimpering for at least 20 minutes and outputs the normalized value as the output data 125.

At step 515, the agent device 103 determines a power level 310 of the battery 127 and identifies a sensor condition 222A-K (hereinafter referred to as "sensor condition 222") corresponding to each of the sensors 115 at the determined power level 310. The sensor condition 222 indicates a pre-defined power level 223 and a threshold value 224.

When the power level 310 has not reached or fallen below the pre-defined power level 223 indicated in the sensor condition 222, the agent device 103 may perform a standard action at step 518. The standard action may cause the agent device 103 to transmit the output data 125 and/or the indication of the output data 125 to the cloud server 109 or the representative device 112.

When the power level 310 meets the pre-defined power level 223 indicated in the sensor condition 222 (e.g., when the power level 310 has reached, exceeds, or fallen below the pre-defined power level 223), the agent device 103 proceeds to step 521 to determine whether the output data 125 for each sensor 115 meets the threshold value 224 defined in the sensor condition 222. Continuing with the example above, the threshold value 224 defined in the sensor condition 222 for the microphone may be a value that can be compared with the output data 125 indicating that the agent was yelping or whimpering for 20 minutes. This comparison indicates whether the agent was in state of pain or discomfort for those 20 minutes, which is sufficient enough to warrant notifying the representative of the agent device 103. If the value of the output data 125 meets or exceeds the threshold value 224, the agent device 103 uploads the output data 125 or an indication of the output data 125 to the cloud server 109 or the representative device 112, at step 524.

However, if the value of the output data 125 does not exceed the threshold value 224, then the agent device 103 determines to use the output data 125 to calculate the aggregate sensor output data 256, at step 527. In an embodiment, the agent device 103 only calculates the aggregate sensor output data 256 when none of the output data 125 from any of the sensors 115 meets the corresponding sensor condition 222. In another embodiment, the agent device 103 calculates the aggregate sensor output data 256 when the output data 125 from at least one of the sensors 115 meets the corresponding sensor condition 222. The agent device 103 computes the aggregate sensor output data 256 according to equation (2) shown and described above. The aggregate sensor output data 256 indicates an overall state of the agent based on the output data 125 of multiple sensors 115, taking into account multiple different features, activities, biometric data, and other attributes of the agent.

At step 530, the agent device 103 determines whether the aggregate sensor output data 256 meets the aggregate condition 259. The aggregate condition 259 defines a pre-defined aggregate threshold value that can be compared with the aggregate sensor output data 256. This comparison indicates whether the agent was in state of overall pain, discomfort, illness, or danger, which is sufficient enough to warrant notifying the representative of the agent device 103. In this case, the agent device 103 determines that the value of aggregate sensor output data 256 meets or exceeds the pre-defined aggregate threshold value. If so, then the agent device 103 uploads the aggregate sensor output data 256 or an indication of the aggregate sensor output data 256 to the cloud server 109 or the representative device 112, at step 524. If not, then agent device 103 determines that the value of aggregate sensor output data 256 does not meet the pre-defined aggregate threshold value. Then, at step 533, the agent device 103 locally stores the output data 125 because the output data 125 does not indicate a condition of the agent sufficiently concerning enough to warrant notifying the representative.

Figure 6:
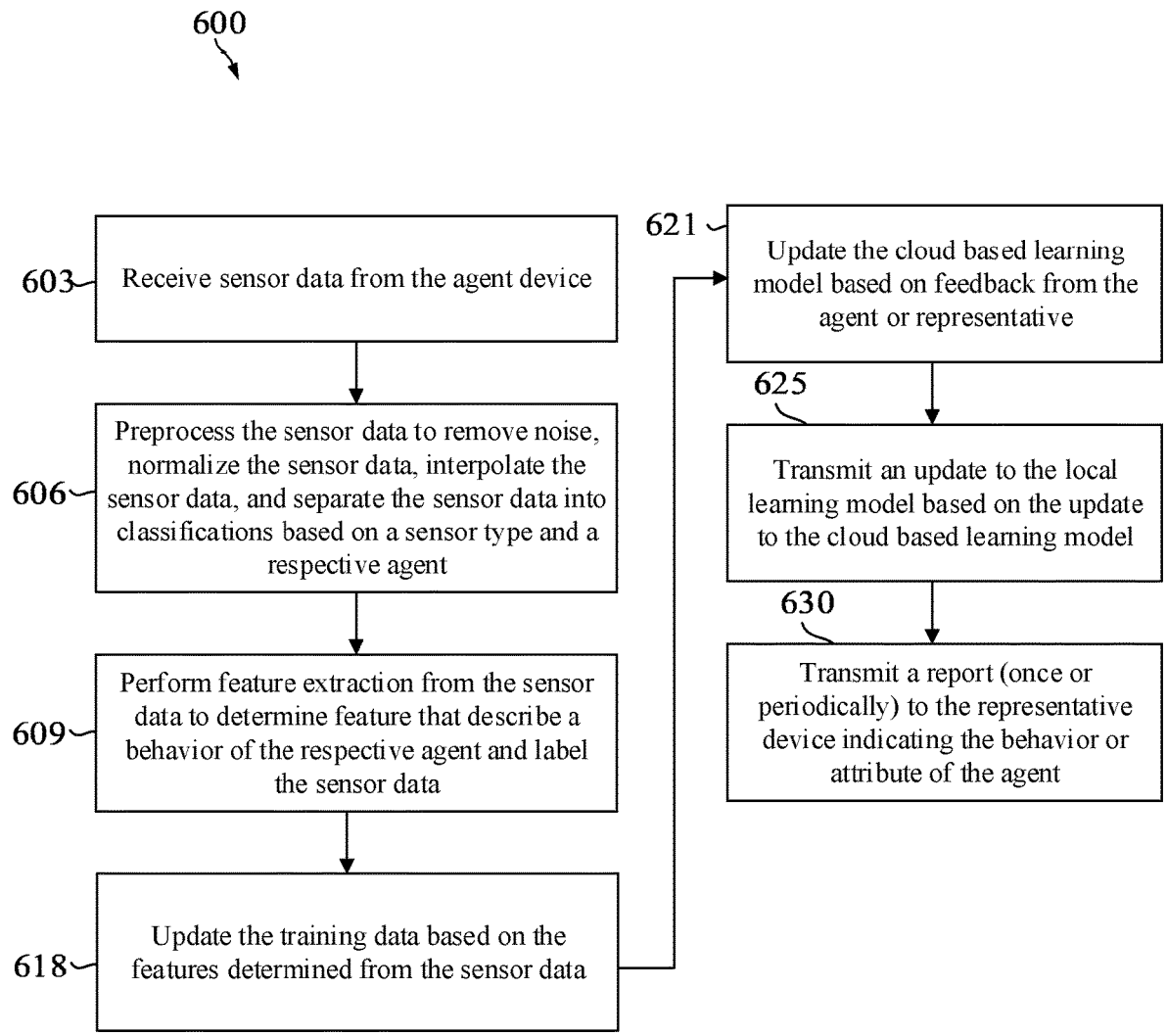
FIG. 6 is flowchart illustrating another method for power efficient monitoring performed by a cloud server of the agent monitoring system according to various embodiments of the disclosure.

FIG. 6 is a flowchart illustrating another method 600 for power efficient monitoring according to various embodiments of the disclosure. In an embodiment, the cloud server 109 performs the method 600 to further develop the cloud based learning model 131. In an embodiment, the agent device 103 may also perform the method 600. In an embodiment, the agent device 103 performs method 600 update the local learning model 122. In an embodiment, the cloud server 109 performs method 600 to create and transmit updates of the local learning model 122 to the agent device 103. In this way, the cloud server 109 performs the heavy computations and stores the data used to create the learning models 122 and 131 on behalf of the agent device 103.

In an embodiment, the cloud based learning model 131 trains two models, a feature embedding model, and decision tree models. As should be appreciated, the cloud based learning model 131 may include other algorithms, models, and methods not otherwise described herein. The feature embedding model converts the raw time series data from the sensor data 118 into a vector in embedded space based on the raw data received from many different agent devices 103. The feature embedding model can be an unsupervised step, in which the data does not need labels. The feature embedding model can also be semi-supervised or supervised, in other embodiments. The decision tree models determine particular conditions or behaviors of the agent, for example, indicating whether an embedded feature is safe/unsafe, healthy/unhealthy, etc. The decision tree models also determine whether an alert is required for the determined condition or behavior of the agent.

The feature embedding model is based on raw data received from many different agent devices 103, and the training of the feature embedding model can be heavily complex. If the feature embedding model is trained by the cloud server 109. The agent device 103 downloads both the feature embedding model and the decision tree models from the cloud server 109. For example, the agent device 103 stores the feature embedding model and the decision tree models in a local memory 250. When the agent device 103 obtains new sensor data 118, the agent device 103 first uses the feature embedding model stored locally to convert the raw time series sensor data 118 to a vector. The agent device 103 labels the sensor data 118 using the decision tree models stored locally.

In cases in which the output data 125 incorrectly predicts a condition or fails to predict a condition, a user, such as the agent or the representative, can provide customized feedback using a graphical user interface on the agent device 103 or the representative device 112. For example, a user may provide feedback user input to the agent device 103 indicating that the agent device 103 incorrectly predicted a condition of the agent. The agent device 103 uses the feedback to update the local decision tree model, for example, by adding a customized second tree that takes the output from a general first tree and the sensor data 118 together as input. The agent device 103 forwards this data (the sensor data 118, the feedback from the user, and/or the update to the local decision tree model) to the cloud server 109.

At step 603, the cloud server 109 and/or the agent device 103 receives the sensor data 118 from multiple different agent devices 103. At this step, the cloud server 109 also receives the data (the sensor data 118, the feedback from the user, and/or the update to the local decision tree model) from the agent device 103. The feedback from the user may be label to the data. In an embodiment, the agent device 103 provides all unlabeled sensor data 118 to the cloud server 109.

At step 606, the cloud server 109 and/or the agent device 103 preprocesses the sensor data 118 to remove the noise, normalize, and interpolate the sensor data 118 in a manner such that the sensor data 118 can be labelled and trained into the cloud based learning model 131. In an embodiment, the cloud server 109 and/or the agent device 103 also separates the received sensor data 118 into classifications, or other applications, based on the sensor 115 from which the sensor data 118 was obtained and an agent that was being monitored by the sensor 115. After completing step 606, the sensor data 118 (Y) for each sensor 115 is represented as $\{Y_1, Y_2, \ldots Y_i, \ldots Y_n\}$.

The cloud based learning model 131 and/or the agent device 103 then receives the sensor data 118 (Y) as input. At step 609, the cloud based learning model 131 performs feature extraction on the sensor data 118 (Y) to determine features that may predict a behavior of the agent. The cloud based learning model 131 then labels the sensor data 118 (Y) according to the determined features.

The feature extraction may be performed using a combination of a decision tree and neural network based learning methods, such as, for example, a deep neural network, a recurrent neural network, a multi-task learning model, a transfer learning model, or any other learning model. For example, the sensor data 118 (Y) may be fed into an encoder for feature embedding, which determines the feature embedded in the sensor data 118 (Y), using the feature embedding model described above.

The features determined from the sensor data 118 (Y) may be represented by a normalized value that can be compared with thresholds to predict behaviors of the agent. After completing step 609, the features (Y) determined by the sensor data 118 (Y) for each sensor 115 is represented as $\{F_1, F_2, \ldots F_i, \ldots F_n\}$.

The cloud server 109 and/or the agent device 103 may store thresholds (T) by which to compare the features (Y) to determine whether the feature (Y) is significant enough to further train the cloud based learning model 131 or report the feature (Y) to the representative of the agent. The thresholds (T) for each of the sensors 115 is represented as $\{T_1, T_2, \ldots T_i, \ldots T_n\}$. The thresholds (T) are pre-defined values that may be input by an operator of the cloud server 109 based on expert data or determined by the cloud based learning model 131 based on a parameter of a classifier and historical data describing the agent.

In an embodiment, the cloud based learning model 131 and/or the agent device 103 compares the features (Y) determined from the sensor data 118 (Y) with the standard data 265 for the sensor 115 or historical data describing the behavior or attribute of the agent to obtain a difference 444. The difference 444 represents a difference between the standard data 265 for the sensor 115 or historical data describing the behavior or attribute of the agent and the features (Y) determined from the sensor data 118 (Y).

In an embodiment, the cloud based learning model 131 and/or the local learning model 122 determines whether the difference 444 is greater than a threshold (T) defined for the sensor 115. If not, then the cloud server 109 performs the standard method of reporting or alerting the representative device 112. If the difference 444 is greater than a threshold (T), then at step 618, the cloud server 109 and the agent device 103 updates the training data 134 based on the features (Y) determined from the sensor data 118 (Y). For example, the training data 134 is updated to reflect a correspondence between the sensor data 118 (Y) and the features (Y).

In addition, at step 621, the cloud server 109 and/or the agent device 103 determines an update to the cloud based learning model 131 and/or the local learning model 122. For example, the update to the local based learning model 123 reflects the determined a behavior or feature of the agent based on the features (Y). In an embodiment, the cloud server 109 uses the feedback from the user and/or the update to the local decision tree model received at step 603 to determine a new decision tree model. The new decision tree model is the update the cloud based learning model 131 that should also be transmitted to the local learning model 122 upon determining the new decision tree model.

At step 625, the cloud server 109 transmits the update to the cloud based learning model 131 to the agent device 103, when the local learning model 131 should be updated. The cloud server 109 may transmit updates, such as the new decision tree model, periodically or based on a predefined schedule to reflect the overall change in feedback received from different users. For example, the updated cloud based learning model 131 can be transmitted to one or more agent devices 103 at the beginning of every month or the beginning of every week. The agent device 103 can refresh the first general tree from the cloud server 109 while still maintaining the customized second tree described above.

The agent device 103 uses the update to the cloud based learning model 131 to update the local learning model 122. The local learning model 122 is also updated to reflect that, when input 303 similar to the sensor data 118 (Y) is received by the local learning model 122, then local learning model 122 may determine a behavior of the agent based on the features (Y).

At step 630, the cloud server 109 may transmit a report to the representative device 112 indicating the behavior of the agent determined using steps 603, 606, 609, 618, and 621 of method 600. The report may comprise a textual or visual indicator of the behavior or attribute of the agent. In an embodiment, the cloud server 109 waits for a scheduled period of time, and then transmits the report indicating multiple determined behaviors or attributes of the agent over a pre-defined period of time. For example, the cloud server 109 may be pre-configured with a schedule that indicates when to send reports to the representative device 112.

Figure 7:
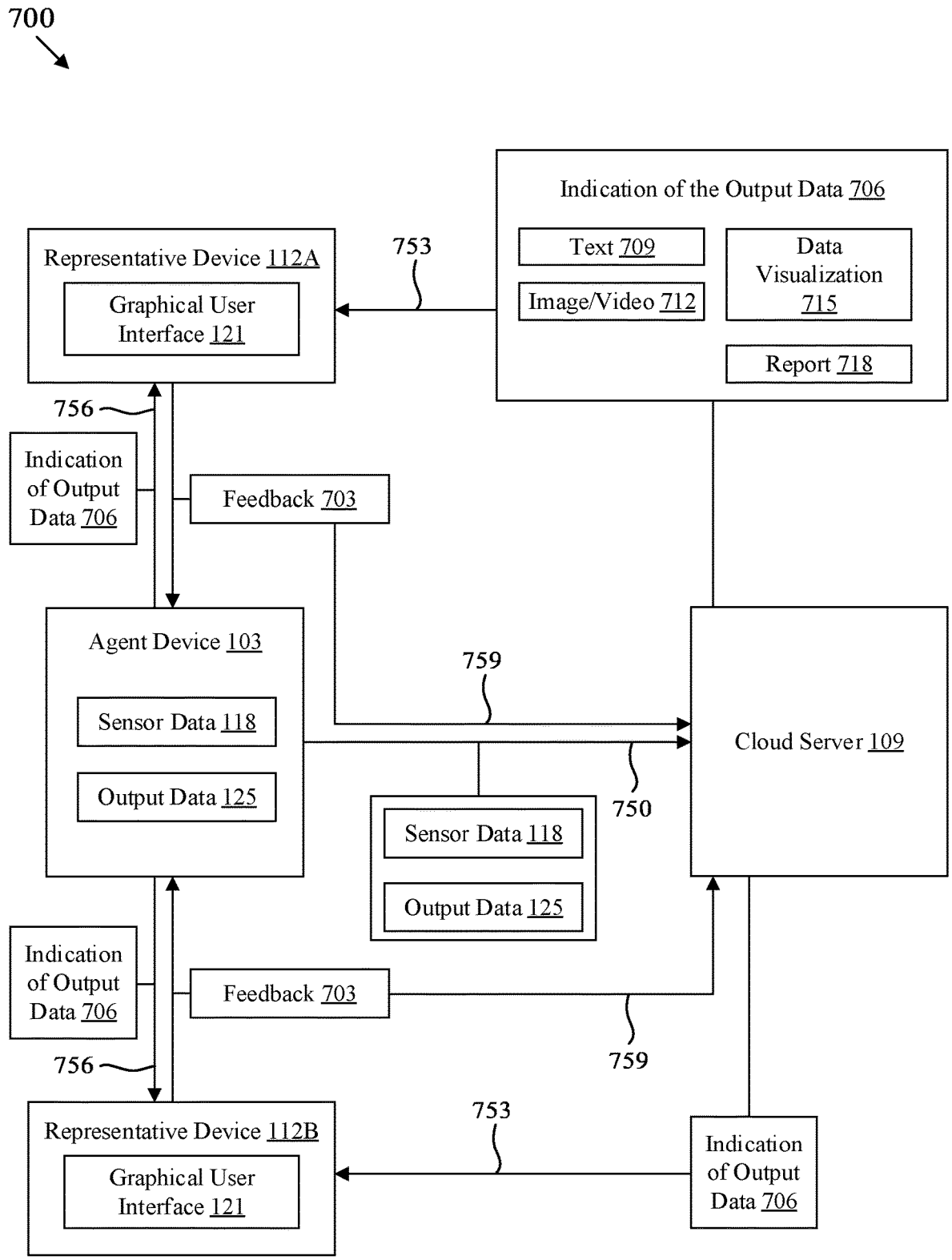
FIG. 7 is a diagram illustrating another agent monitoring system according to various embodiments of the disclosure.

FIG. 7 is a diagram illustrating an agent monitoring system 700 according to various embodiments of the disclosure. The agent monitoring system 700 includes the agent device 103, the cloud server 109, and two representative devices 112A and 112B. Specifically, FIG. 7 shows the transmission of information between the agent device 103, the cloud server 109, and two representative devices 112A and 112B in the agent monitoring system 700.

In the example shown in FIG. 7, the same agent may be associated with two different representatives, and thus, each of the representatives have different representative devices 112A and 112B. For example, when the agent is an elderly patient, one representative device 112A belongs to a family member of the agent, and the other representative device 112B belongs to a physician of the agent.

As shown by FIG. 7, the agent device 103 maintains the sensor data 118 detected by the sensors 115 (not shown) of the agent device 103 and generates the output data 125 based on the sensor data 118. At arrow 750, the agent device 103 uploads the sensor data 118 and/or the output data 125 to the cloud server 109 based on the steps of method 500 described above with reference to FIG. 5.

In an embodiment, the cloud server 109 obtains, or generates, an indication 706 of the output data 125 after receiving the output data 125 from the agent device 103. The indication 706 of the output data 125 describes the predicted condition of the agent that is described by the output data 125. When the output data 125 is in the form of a normalized numerical value, the cloud server 109 determines the predicted condition of the agent corresponding to the numerical value. The cloud server 109 then generates an indication 706 of the predicted condition of the agent corresponding to the output data 125.

In some embodiments, the indication 706 may be in the form of text 709, which textually represents the predicted condition of the agent. For example, if the output data 125 indicates that the agent is experiencing a temperature of 99 degrees (°) for an hour, then the cloud server 109 generates text reciting, for example, "Warning: Temperature has been 99° for an hour."

The indication 706 may be in the form of an image or video 712. For example, if the output data 125 indicates that the agent is located in a potentially hazardous area, then the cloud server 109 uses the sensor data 118 to extract an image or video showing the potentially hazardous area.

The indication 706 may be in the form of a data visualization 715, which may be, for example, a graph, a location frequency map, plot, or any other information graphic that represents the output data 125. For example, the data visualization 715 may show a graph indicating a sleep level of the agent over the course of 8 hours.

The indication 706 may also be in the form of a report 718, indicating multiple different output data 125 over a longer period of time. For example, the report 718 may indicate the sleep level of the agent over the course of the week, instead of just one night. As should appreciated, there may be other methods of indicating the output data 125 that is not otherwise shown or described with reference to FIG. 7.

As shown by arrows 753, the cloud server 109 transmits the indication 706 of the output data 125 to the representative devices 112A and 112B. In some cases, the indication 706 of the output data 125 sent to representative device 112A may be different from the indication 706 of the output data 125 sent to representative device 112B. For example, since the representative device 112B belongs to a physician of the agent, the cloud server 109 only transmits information describing health related output data 125 to the physician's representative device 112B. In this case, the indication 706 of the output data 125 sent to representative device 112B only describes health related conditions and behaviors of the agent. In contrast, the representative device 112B belonging to the family member of the agent receives an indication 706 of all the output data 125 of the agent device 103.

Upon receiving the indication 706 of the output data 125, the representative devices 112A and 112B display the indication 706 of the output data 125 using the graphical user interface 121. The representative interacts with the graphical user interface 121 to retrieve additional data regarding the agent, as needed. In an embodiment, the representative provides a user input to the graphical user interface 121 indicating feedback 703 to the agent monitoring system 700. For example, the feedback 703 may indicate whether the output data 125 indicated in the graphical user interface 121 is significant, accurate, or relevant to the representative. The feedback 703 may otherwise indicate any other helpful guidance regarding the determination of the output data 125. For example, when the indication 706 of the output data 125 indicates that the heart rate of the agent is higher every morning, the representative may provide feedback 703 through the graphical user interface 121 indicating that this higher heart rate is normal behavior for the agent during this period of time.

As shown by arrows 759, the representative devices 112A and 112B transmit this feedback 703 back to the cloud server 109. The cloud server 109 may update the cloud based learning model 131 based on the received feedback 703 to ignore the heart rate change of the agent in the morning. The cloud server 109 transmits this update to the agent device 103 to enable the agent device 103 to update the local learning model 122.

In some cases, the agent device 103 obtains, or generates, the indication 706 of the output data 125 and transmits the indication 706 of the output data 125 directly to the representative devices 112A and/or 112B. As shown by arrows 756, the agent device 103 transmits the indication 706 of the output data 125 to the representative devices 112A and 112B. As described above, the indication 706 of the output data 125 sent to representative device 112A may be different from the indication 706 of the output data 125 sent to representative device 112B.

Figure 8:
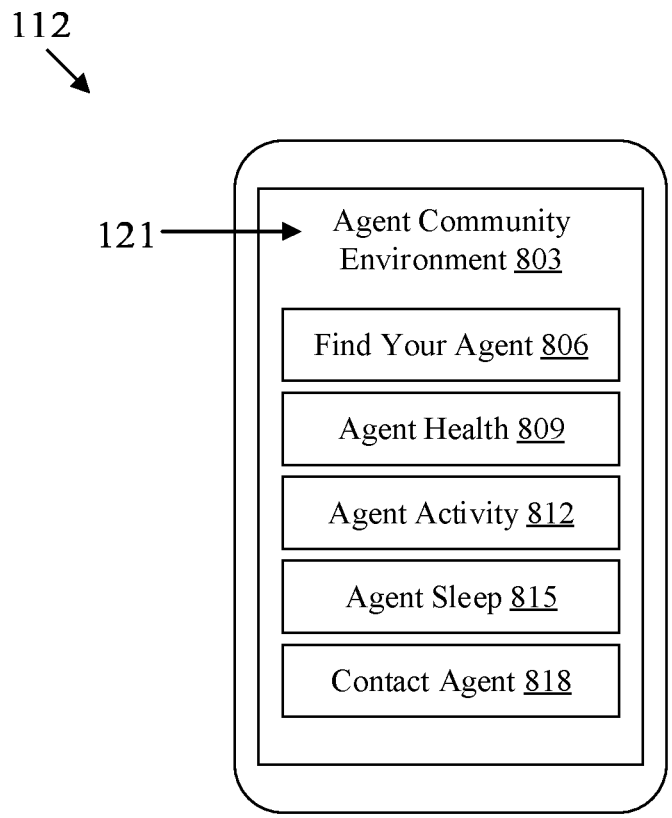
FIG. 8 is a diagram illustrating a graphical user interface of a representative device in the agent monitoring system according to various embodiments of the disclosure.

FIG. 8 is a diagram illustrating the graphical user interface 121 of the representative device 112A-B (hereinafter referred to as "representative device 112") according to various embodiments of the disclosure. As shown by FIG. 8, the graphical user interface 121 displays an agent community environment 803. The agent community environment 803 may be associated with an application that may be installed in an application marketplace. The representative using the representative device 112 interacts with the agent community environment 803 displayed on the graphical user interface 121.

As shown by FIG. 8, the agent community environment 803 includes multiple selectable buttons, which may include a link to a different application page or a pop-up page that displays information related to the agent wearing the agent device 103. In the example shown in FIG. 8, the selectable buttons include a find your agent button 806, an agent health button 809, an agent activity button 812, an agent sleep button 815, and a contact agent button 818. As should be appreciated, the agent community environment 803 may include other links not otherwise shown in FIG. 8.

When the representative selects the find your agent button 806, the graphical user interface 121 displays a map indicating a current location of the agent wearing the agent device 103 (not shown). When the representative selects the agent health button 809, the graphical user interface 121 displays, for example, a data visualization of the health of the agent. The data visualization may be specific to a particular health indicator (e.g., temperature, heart rate, pulse, blood sugar, etc.), or generalized. When the representative selects the agent activity button 812, the graphical user interface 121 displays, for example, a data visualization of the physical activity or calorie burn of the agent over a period of time. When the representative selects the agent sleep button 815, the graphical user interface 121 displays, for example, a data visualization of a sleep quality of the agent's previous night of sleep. When the representative selects the contact agent button 818, the representative device 112 initiates a voice call, data call, text message, video chat, or other method of communicating with the agent device 103 over the network 106.

Figure 9:
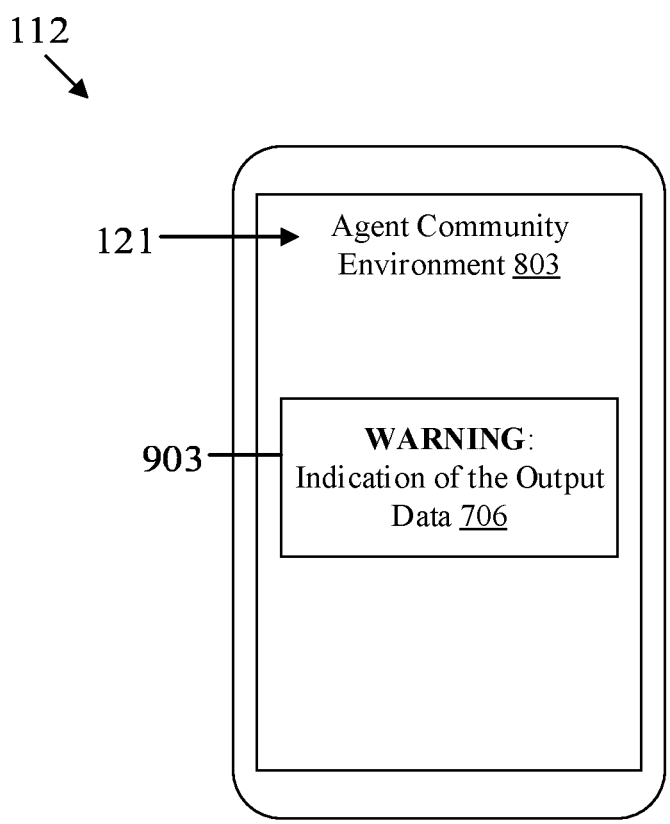
FIG. 9 is a diagram illustrating the graphical user interface of the representative device according to various embodiments of the disclosure.

FIG. 9 is a diagram illustrating the graphical user interface 121 of the representative device 112 according to various embodiments of the disclosure. In an embodiment, the representative device 112 receives an indication 706 of the output data 125 based on the method 500 described above with reference to FIG. 5. Upon receiving the indication 706 of the output data 125, the representative device 112 generates a pop up notification button 903 that clearly presents the indication 706 of the output data 125 to the representative. In an embodiment, the representative may select the pop up notification button 903 to access additional data regarding the output data 125.

Figure 10:
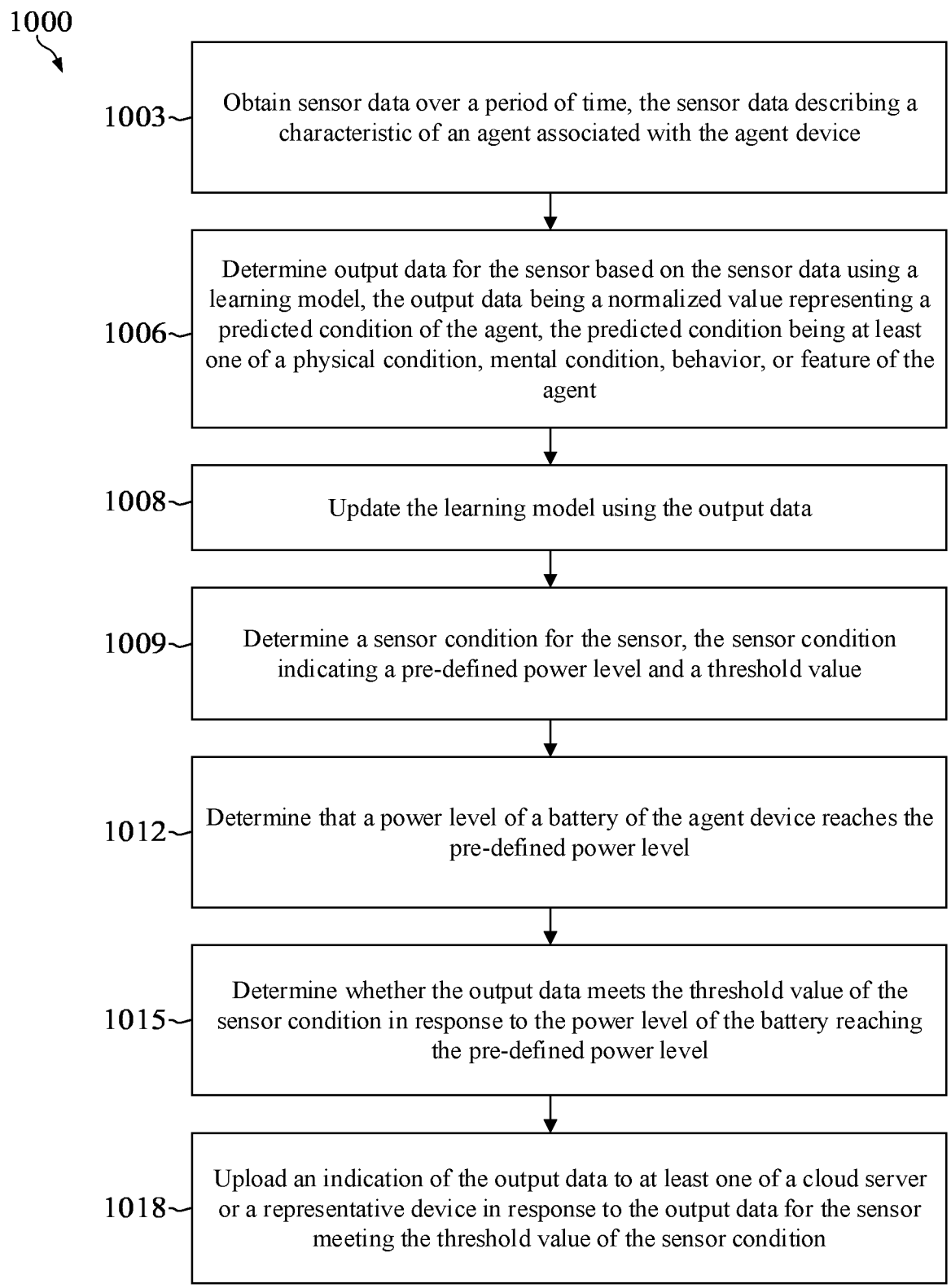
FIG. 10 is flowchart illustrating a method for power efficient monitoring according to various embodiments of the disclosure.

FIG. 10 is flowchart illustrating a method 1000 for power efficient monitoring according to various embodiments of the disclosure. The agent device 103 performs method 1000 after the sensors 115 have been powered on to detect sensor data 118. At step 1003, the sensor 115 obtains (e.g., detects) sensor data 118 over a period of time. The sensor data 118 describes a characteristic of the agent associated with (e.g., wearing or carrying) the agent monitoring device 103.

At step 1006, the agent device 103 determines output data 125 for the sensor 115 based on the sensor data 118 using the local learning model 122. The output data 125 is a normalized value representing a predicted condition of the agent. The predicted condition of the agent is at least one of a physical condition, mental condition, behavior, or feature of the agent. At step 1008, the agent device 103 updates the local learning model 122 using the output data 125.

At step 1009, the agent device 103 determines a sensor condition 222 for the sensor 115. The sensor condition 222 indicates a pre-defined power level 223 and a threshold value 224.

At step 1012, the agent device 103 determines that a power level 310 of the battery 127 of the agent device 103 reaches the pre-defined power level 223. At step 1015, the agent device 103 determines whether the output data 125 meets the threshold value 224 of the sensor condition 222 in response to the power level 310 of the battery 127 reaching the pre-defined power level 223. At step 1018, the agent device 103 uploads the indication 706 of the output data 125 to at least one of the cloud server 109 or one or more representative devices 112 in response to the output data 125 meeting the threshold value 224 of the sensor condition 222.

Figure 11:
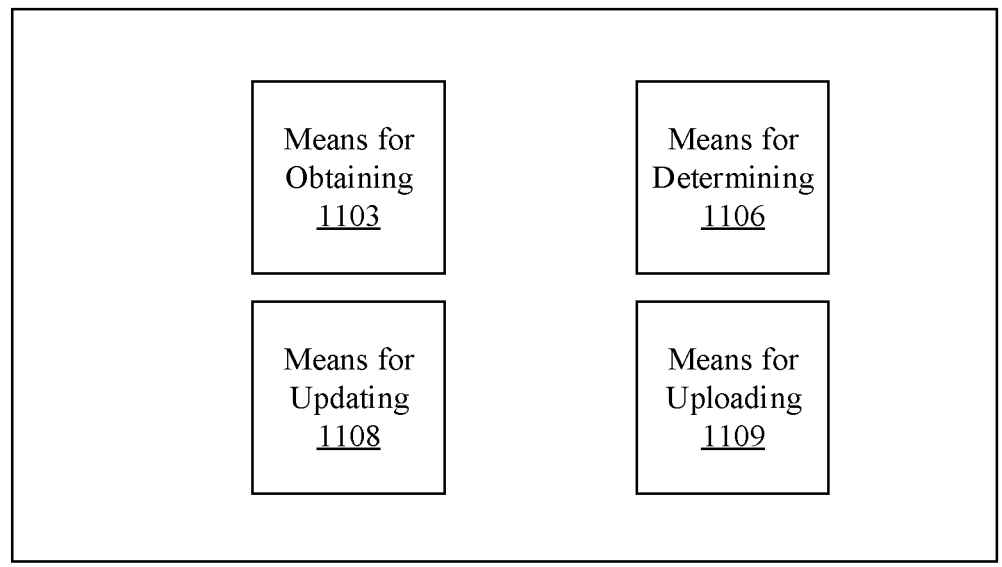
FIG. 11 is a diagram illustrating an apparatus for implementing the method of FIG. 10 according to various embodiments of the disclosure.

FIG. 11 is a diagram illustrating an apparatus 1100 for implementing the method 1000 of FIG. 10 according to various embodiments of the disclosure. The apparatus 1100 comprises a means for obtaining 1103 sensor data 118 over a period of time. The sensor data 118 describes a characteristic of the agent associated with (e.g., wearing or carrying) the agent monitoring device 103. The apparatus 1100 comprises a means for determining 1106 a sensor condition 222 for the sensor 115. The output data 125 is a normalized value representing a predicted condition of the agent. The means for determining 1106 also includes a means for determining 1106 a sensor condition 222 for the sensor 115. The sensor condition 222 indicates a pre-defined power level 223 and a threshold value 224. The means for determining 1106 also includes a means for determining 1106 that a power level 310 of the battery 127 of the agent device 103 reaches the pre-defined power level 223. The means for determining 1106 also includes a means for determining 1106 whether the output data 125 meets the threshold value 224 of the sensor condition 222 in response to the power level 310 of the battery 127 reaching the pre-defined power level 223. The apparatus 1000 also includes a means for updating 1108 the local learning model 122 using the output data 125. The apparatus 1100 also includes a means for uploading 1109 the indication 706 of the output data 125 to at least one of the cloud server 109 or one or more representative devices 112 in response to the output data 125 meeting the threshold value 224 of the sensor condition 222.

While several embodiments have been provided in the present disclosure, it should be understood that the disclosed systems and methods might be embodied in many other specific forms without departing from the spirit or scope of the present disclosure. The present examples are to be considered as illustrative and not restrictive, and the intention is not to be limited to the details given herein. For example, the various elements or components may be combined or integrated in another system or certain features may be omitted, or not implemented.

In addition, techniques, systems, subsystems, and methods described and illustrated in the various embodiments as discrete or separate may be combined or integrated with other systems, modules, techniques, or methods without departing from the scope of the present disclosure. Other items shown or discussed as coupled may be directly coupled or may be indirectly coupled or communicating through some interface, device, or intermediate component whether electrically, mechanically, or otherwise. Other examples of changes, substitutions, and alterations are ascertainable by one skilled in the art and could be made without departing from the spirit and scope disclosed herein.

What is claimed is:

1. A method implemented by an agent monitoring device, comprising:
   obtaining sensor data over a period of time by a sensor of the agent monitoring device, the sensor data describing a characteristic of an agent associated with the agent monitoring device;
   determining output data for the sensor based on the sensor data using a learning model, the output data being a value representing a predicted condition of the agent, the predicted condition being at least one of a physical condition, mental condition, behavior, or feature of the agent;
   updating the learning model using the output data;
   determining a sensor condition for the sensor, the sensor condition indicating a pre-defined power level and a threshold value associated with the predicted condition of the agent;
   determining that a power level of a battery of the agent monitoring device meets the pre-defined power level;
   determining whether the output data meets the threshold value associated with the predicted condition of the agent in the sensor condition in response to the power level of the battery having reached the pre-defined power level; and
   uploading an indication of the output data to at least one of a cloud server or a representative device in response to the output data for the sensor having met the threshold value associated with the predicted condition of the agent in the sensor condition.

2. The method of claim 1, wherein the learning model is based on a long short term memory (LSTM) architecture and on training data describing a behavior of a plurality of different agents similar to the agent, wherein the method further comprises:
   receiving an update to the learning model from a cloud server, wherein the update to the learning model is based on the training data; and
   updating the learning model based on the update to the learning model to improve an accuracy of the learning model, wherein the sensor data is an input of the learning model, and wherein the output data is an output of the learning model.

3. The method of claim 1, wherein the method further comprises:
   determining whether the power level of the battery meets a second pre-defined power level; and
   wherein, in response to the power level of the battery having reached the second pre-defined power level, the method further comprises powering off the sensor.

4. The method of claim 1, wherein the method further comprises:
   determining standard data for the sensor, the standard data indicating a baseline behavior of the agent,
   wherein, in response to the power level of the battery having reached the pre-defined power level, the method further comprises:
      computing a difference between the output data and the standard data for the sensor; and
      uploading the output data to at least one of the cloud server or the representative device in response to the difference between the output data and the standard data having met the sensor condition.

5. The method of claim 1, wherein, after obtaining the sensor data over the period of time and before determining the output data, the method further comprises:
   filtering the sensor data to remove noise unrelated to the agent; and
   performing normalization and interpolation of the sensor data.

6. The method of claim 1, wherein the agent monitoring device comprises a plurality of sensors that are each configured to detect a different type of sensor data, wherein the plurality of sensors include at least one of a Global Positioning System (GPS) locator, a BLUETOOTH device, a microphone, a thermometer, or a heart rate monitor, and wherein the different type of sensor data describes at least one of a temperature of the agent, a pulse of the agent, a calorie burn of the agent, a heart rate of the agent, a respiration activity of the agent, a physical activity of the agent, a sound emitted by the agent, a posture of the agent, a sleep activity of the agent, a GPS location of the agent, or a light surrounding the agent.

7. The method of claim 1, wherein the learning model is based on training data describing a behavior of a plurality of different agents similar to the agent and a set of demographics describing the agent, and wherein the set of demographics being at least one of a species, an age, or a gender of the agent.

8. The method of claim 6, wherein each of the sensors is associated with a respective sensor condition, wherein the method further comprises:
   obtaining different sensor data from each of the sensors; and
   determining output data for each of the sensors using the learning model;
   wherein, in response to the power level of the battery having reached the pre-defined power level, the method further comprises:
      determining that none of the output data for the sensors meets the respective sensor condition;
      determining aggregate sensor output data based on the output data for each of the sensors, a sensor weight for each of the sensors, a difference between sensor output data for each of the sensors and a standard data for each of the sensors; and
      uploading an indication of the aggregate sensor output data to at least one of the cloud servers or the representative device in response to the aggregate sensor output data having met an aggregate condition.

9. An agent monitoring device, comprising:
   a sensor configured to obtain sensor data over a period of time, the sensor data describing a characteristic of an agent associated with the agent monitoring device;
   a memory configured to store instructions; and
   a processor coupled to the memory and configured to execute the instructions, which cause the processor to be configured to:
      determine output data for the sensor based on the sensor data using a learning model, the output data being a normalized value representing a predicted condition of the agent, the predicted condition being at least one of a physical condition, mental condition, behavior, or feature of the agent;
      update the learning model using the output data;
      determine a sensor condition for the sensor, the sensor condition indicating a pre-defined power level and a threshold value associated with the predicted condition of the agent;
      determine that a power level of a battery of the agent monitoring device meets the pre-defined power level;

determine whether the output data meets the threshold value associated with the predicted condition of the agent in the sensor condition in response to the power level of the battery having reached the pre-defined power level; and upload an indication of the output data to at least one of a cloud server or a representative device in response to the output data for the sensor having met the threshold value associated with the predicted condition of the agent in the sensor condition.

10. The agent monitoring device of claim 9, wherein the learning model is based on a long short term memory (LSTM) architecture and on training data describing a behavior of a plurality of different agents similar to the agent, wherein the instructions further cause the processor to be configured to:

receive an update to the learning model from a cloud server, wherein the update to the learning model is based on the training data; and update the learning model based on the update to the learning model to improve an accuracy of the learning model, wherein the sensor data is an input of the learning model, and wherein the output data is an output of the learning model.

11. The agent monitoring device of claim 9, wherein the instructions further cause the processor to be configured to:

determine whether the power level of the battery meets a second pre-defined power level; and wherein, in response to the power level of the battery having reached the second pre-defined power level, the instructions further cause the processor to be configured to power off the sensor.

12. The agent monitoring device of claim 9, wherein the instructions further cause the processor to:

determine standard data for the sensor, the standard data indicating a baseline behavior of the agent, and wherein, in response to the power level of the battery having reached the pre-defined power level, the instructions further cause the processor to be configured to:

compute a difference between the output data and the standard data for the sensor, and wherein the memory is configured to store the output data in response to the difference between the output data and the standard data failing to meet the sensor condition.

13. The agent monitoring device of claim 9, wherein the instructions further cause the processor to be configured to:

filter the sensor data to remove noise unrelated to the agent; and perform normalization and interpolation of the sensor data.

14. The agent monitoring device of claim 9, wherein the agent monitoring device comprises a plurality of sensors that are each configured to detect a different type of sensor data, wherein the plurality of sensors comprise at least one of a Global Positioning System (GPS) locator, a BLUETOOTH device, a microphone, a thermometer, or a heart rate monitor, and wherein the different type of sensor data describes at least one of a temperature of the agent, a pulse of the agent, a calorie burn of the agent, a heart rate of the agent, a respiration activity of the agent, a physical activity of the agent, a sound emitted by the agent, a posture of the agent, a sleep activity of the agent, a GPS location of the agent, or a light surrounding the agent.

15. A computer program product comprising computer-executable instructions for storage on a non-transitory computer-readable medium that, when executed by a processor, cause an agent monitoring device to:

obtain sensor data over a period of time, the sensor data describing a characteristic of an agent associated with the agent monitoring device;

determine output data for the sensor based on the sensor data using a learning model, the output data being a normalized value representing a predicted condition of the agent, the predicted condition being at least one of a physical condition, mental condition, behavior, or feature of the agent;

update the learning model using the output data;

determine a sensor condition for the sensor, the sensor condition indicating a pre-defined power level and a threshold value associated with the predicted condition of the agent;

determine that a power level of a battery of the agent monitoring device meets the pre-defined power level;

determine whether the output data meets the threshold value associated with the predicted condition of the agent in the sensor condition in response to the power level of the battery having reached the pre-defined power level; and upload an indication of the output data to at least one of a cloud server or a representative device in response to the output data for the sensor having met the threshold value associated with the predicted condition of the agent in the sensor condition.

16. The computer program product of claim 15, wherein the learning model is based on a long short term memory (LSTM) architecture and on training data describing a behavior of a plurality of different agents similar to the agent, wherein the computer-executable instructions further cause the agent monitoring device to:

receive an update to the learning model from a cloud server, wherein the update to the learning model is based on the training data; and update the learning model based on the update to the learning model to improve an accuracy of the learning model, wherein the sensor data is an input of the learning model, and wherein the output data is an output of the learning model.

17. The computer program product of claim 15, wherein the computer-executable instructions further cause the agent monitoring device to:

determine whether the power level of the battery meets a second pre-defined power level; and wherein, in response to the power level of the battery having reached the second pre-defined power level, the computer-executable instructions further cause the agent monitoring device to power off the sensor.

18. The computer program product of claim 15, wherein the computer-executable instructions further cause the agent monitoring device to:

determine standard data for the sensor, the standard data indicating a baseline behavior of the agent, wherein, in response to the power level of the battery having reached the pre-defined power level, the computer-executable instructions further cause the agent monitoring device to:

compute a difference between the output data and the standard data for the sensor; and upload the indication of the output data to at least one of the cloud server or the representative devices in response to the difference between the output data and the standard data having met the sensor condition.

19. The computer program product of claim 15, wherein the agent monitoring device comprises a plurality of sensors that are each configured to detect a different type of sensor data, wherein the plurality of sensors comprise at least one of a Global Positioning System (GPS) locator, a BLUETOOTH device, a microphone, a thermometer, or a heart rate monitor, and wherein the different type of sensor data describes at least one of a temperature of the agent, a pulse of the agent, a calorie burn of the agent, a heart rate of the agent, a respiration activity of the agent, a physical activity of the agent, a sound emitted by the agent, a posture of the agent, a sleep activity of the agent, a GPS location of the agent, or a light surrounding the agent.

20. The computer program product of claim 15, wherein each of the sensors is associated with a respective sensor condition, wherein the computer-executable instructions further cause the agent monitoring device to:

obtain different sensor data from each of the sensors; and
determine output data for each of the sensors using the learning model;
wherein, in response to the power level of the battery having reached the pre-defined power level, the computer-executable instructions further cause the agent monitoring device to:
determine that none of the output data for the sensors meets the respective sensor condition;
determine aggregate sensor output data based on the output data for each of the sensors, a sensor weight for each of the sensors, a difference between sensor output data for each of the sensors and a standard data for each of the sensors; and
upload an indication of the aggregate sensor output data to at least one of the cloud server or the representative device in response to the aggregate sensor output data having met an aggregate condition.

* * * * *

UNITED STATES PATENT AND TRADEMARK OFFICE
CERTIFICATE OF CORRECTION

PATENT NO. : 12,431,242 B2  
APPLICATION NO. : 18/177059  
DATED : September 30, 2025  
INVENTOR(S) : Jialing Wu et al.

Page 1 of 1

It is certified that error appears in the above-identified patent and that said Letters Patent is hereby corrected as shown below:

On the Title Page

Item (71) Applicant: Delete "Huawei Technologies Co., Ltd., Guangdong (CN)" and insert -- Huawei Technologies Co., Ltd., Shenzhen (CN) --.

Signed and Sealed this  
Ninth Day of December, 2025

John A. Squires  
*Director of the United States Patent and Trademark Office*